United States Patent
Dinsmore et al.

(10) Patent No.: US 7,692,017 B2
(45) Date of Patent: Apr. 6, 2010

(54) QUINOLINE POTASSIUM CHANNEL INHIBITORS

(75) Inventors: Christopher J. Dinsmore, Newton, MA (US); Jeffrey M. Bergman, Sellersville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1035 days.

(21) Appl. No.: 10/571,841

(22) PCT Filed: Sep. 17, 2004

(86) PCT No.: PCT/US2004/030485
§ 371 (c)(1),
(2), (4) Date: Mar. 15, 2006

(87) PCT Pub. No.: WO2005/030129
PCT Pub. Date: Apr. 7, 2005

(65) Prior Publication Data
US 2007/0043042 A1    Feb. 22, 2007

Related U.S. Application Data

(60) Provisional application No. 60/505,202, filed on Sep. 23, 2003.

(51) Int. Cl.
C07D 215/00 (2006.01)
C07D 215/38 (2006.01)
C07D 215/12 (2006.01)

(52) U.S. Cl. .................. 546/157; 546/159; 546/176

(58) Field of Classification Search .................. 546/157, 546/159, 176
See application file for complete search history.

(56) References Cited

FOREIGN PATENT DOCUMENTS

| | | |
|---|---|---|
| EP | 0446604 | 9/1991 |
| WO | WO 02/24686 | 3/2002 |

OTHER PUBLICATIONS

Meltzer, P. C. .et al. STN Accession No. 1978:169926 Document No. 88:169926, Abstract of Tetrahedron (1977), 33(22), 2965-7.*
Bhatt et al. STN Accession No. 1986:168331 Document No. 104:168331, Abstract of Zeitschrift fuer Naturforschung, Teil B: Anorganische Chemie, Organische Chemie (1985), 40B(7), 990-5.*
Bhat et al., Database CA, Chemical Abstracts Service, Columbus, Ohio; "Grignard reaction of 2-substituted-3-cyanoquinolines", XP-002519796, Database accession No. 1986:168331, Zeitschrift Fuer Naturforschung, Teil B: Anorganische Chemie, Organische Chemie (1985) 40B(7), pp. 990-995.
Neelima et al., Database CA, Chemical Abstracts Service, Columbus, Ohio: "Possible pregnancy interceptive agents. Syntheses of 6,7-dimethoxy-2,3,4-trisubstituted-quinolines and 3-cyano-6,7-dimethoxy-2,4-disubstituted-1,4-dihydroquinolines",
XP-002519797, Database accession No. 1987:196231, Indian Journal of Chemistry, Section B: Organic Chemistry, Including Medicinal Chemistry (1986) 25B(9), pp. 939-944.

* cited by examiner

*Primary Examiner*—D. Margaret Seaman
*Assistant Examiner*—Nizal S Chandrakumar
(74) *Attorney, Agent, or Firm*—Heidi M. Struse; Mark R. Daniel; Richard S. Parr

(57) ABSTRACT

The present invention relates to compounds having the structure (I) useful as potassium channel inhibitors to treat cardiac arrhythmias, and the like.

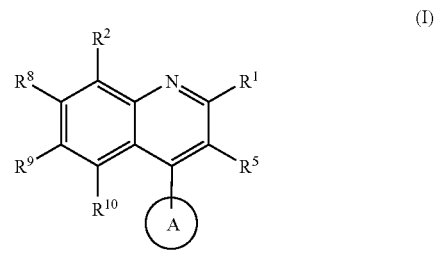

3 Claims, No Drawings

QUINOLINE POTASSIUM CHANNEL INHIBITORS

CROSS REFERENCE TO RELATED APPLICATION

This application is a U.S. National Phase application under 35 U.S.C. §371 of PCT Application No. PCT/US2004/030485, filed Sep. 17, 2004, which claims priority under 35 U.S.C. §119(e) from U.S. Provisional Application Ser. No. 60/505,202, filed Sep. 23, 2003.

BACKGROUND OF THE INVENTION

The present invention relates broadly to compounds that are useful as potassium channel inhibitors. Compounds in this class may be useful as Kv1.5 antagonists for treating and preventing cardiac arrhythmias, and the like, and as Kv1.3 inhibitors for treatment of immunosuppression, autoimmune diseases, and the like.

Voltage gated potassium channels (Kv) are multimeric membrane proteins composed of four α subunits and are often associated with accessory β subunits. Kv channels are typically closed at resting membrane potentials, but open upon membrane depolarization. They are involved in the repolarization of the action potential and thus in the electrical excitability of nerve and muscle fibers. The Kv1 class of potassium channels is comprised of at least seven family members, named Kv1.1, Kv1.3, Kv1.5, etc. Functional voltage-gated K$^+$ channels may exist either as homo-oligomers composed of identical subunits, or hetero-oligomers of different subunit composition. This phenomenon is thought to account for the wide diversity of K$^+$ channels. However, subunit compositions of native K$^+$ channels and the physiologic role that particular channels play are, in most cases, still unclear.

The Kv1.3 voltage-gated potassium channel is found in neurons, blood cells, osteoclasts and T-lymphocytes. Membrane depolarization by Kv1.3 inhibition has been shown to be an effective method to prevent T-cell proliferation and therefore has applications in many autoimmune conditions. Inhibition of K$^+$ channels in the plasma membrane of human T-lymphocytes has been postulated to play a role in eliciting immunosuppressive responses by regulating intracellular Ca$^{++}$ homeostasis, which has been found to be important in T-cell activation. Blockade of the Kv1.3 channel has been proposed as a novel mechanism for eliciting an immunosuppressant response (Chandy et al., *J. Exp. Med.* 160: 369, 1984; Decoursey et al., *Nature*, 307: 465, 1984). However, the K$^+$ channel blockers employed in these early studies were non-selective. In later studies, Margatoxin, which blocks only Kv1.3 in T-cells, was shown to exhibit immunosuppressant activity in both in vitro and in vivo models. (Lin et al., *J. Exp. Med*, 177: 637, 1993). The therapeutic utility of this compound, however, is limited by its potent toxicity. Recently, a class of compounds has been reported that may be an attractive alternative to the above-mentioned drugs (U.S. Pat. Nos. 5,670,504; 5,631,282; 5,696,156; 5,679,705; and 5,696,156). While addressing some of the activity/toxicity problems of previous drugs, these compounds tend to be of large molecular weight and are generally produced by synthetic manipulation of a natural product, isolation of which is cumbersome and labor intensive.

Atrial fibrillation (AF) is the most common sustained cardiac arrhythmia in clinical practice and is likely to increase in prevalence with the aging of the population. Conservative estimates indicate that AF affects >2 million Americans, represents over 5% of all admissions for cardiovascular diseases and leads to a 3- to 5-fold increase in the risk of stroke (Kannel et al, *Am. J. Cardiol.*, 82:2N-9 N, 1998). While AF is rarely fatal, it can impair cardiac function and lead to complications such as the development of congestive heart failure, thromboembolism, or ventricular fibrillation.

Reentrant excitation (reentry) has been shown to be a prominent mechanism underlying supraventricular arrhythmias in man (Nattel, S., *Nature,* 415:219-226, 2002). Reentrant excitation requires a critical balance between slow conduction velocity and sufficiently brief refractory periods to allow for the initiation and maintenance of multiple reentry circuits to coexist simultaneously and sustain AF. Increasing myocardial refractoriness by prolonging action potential duration (APD) prevents and/or terminates reentrant arrhythmias. Action potential duration is determined by the contributions of the repolarizing potassium currents $I_{Kr}$, $I_{KS}$, and $I_{Kur}$, and the transient outward current, $I_{to}$. Blockers of any one of these currents would therefore be expected to increase the APD and produce antiarrhythmic effects.

Currently available antiarrhythmic agents have been developed for the treatment of ventricular and atrial/supraventricular arrhythmias. Malignant ventricular arrhythmias are immediately life-threatening and require emergency care. Drug therapy for ventricular arrhythmia includes Class Ia (eg. procainamide, quinidine), Class Ic (eg. flecainide, propafenone), and Class III (amiodarone) agents, which pose significant risks of proarrhythmia. These Class I and III drugs have been shown to convert AF to sinus rhythm and to prevent recurrence of AF (Mounsey, J P, DiMarco, J P, *Circulation,* 102:2665-2670), but pose an unacceptable risk of potentially lethal ventricular proarrhythmia and thus may increase mortality (Pratt, C M, Moye, L A, *Am J. Cardiol.,* 65:20B-29B, 1990; Waldo et al, *Lancet,* 348:7-12, 1996; Torp-Pedersen et al, *Expert Opin. Invest. Drugs,* 9:2695-2704, 2000). These observations demonstrate a clear unmet medical need to develop safer and more efficacious drugs for the treatment of atrial arrhythmias.

Class III antiarrhythmic agents cause a selective prolongation of the APD without significant depression of cardiac conduction or contractile function. The only selective Class III drug approved for clinical use in atrial fibrillation is dofetilide, which mediates its anti-arrhythmic effects by blocking $I_{Kr}$, the rapidly activating component of $I_K$ found in both atrium and ventricle in humans (Mounsey, J P, DiMarco, J P, *Circulation,* 102:2665-2670). Since $I_{Kr}$ blockers increase APD and refractoriness both in atria and ventricle without affecting conduction per se, theoretically they represent potentially useful agents for the treatment of arrhythmias like AF (Torp-Pedersen, et al, *Expert Opin. Invest. Drugs,* 9:2695-2704, 2000). However, these agents have the major liability of an enhanced risk of proarrhythmia at slow heart rates. For example, torsades de points has been observed when these compounds are utilized (Roden, D. M. "Current Status of Class III Antiarrhythmic Drug Therapy", *Am J. Cardiol.,* 72:44B49B, 1993). This exaggerated effect at slow heart rates has been termed "reverse frequency-dependence", and is in contrast to frequency-independent or forward frequency-dependent actions (Hondeghem, L. M. "Development of Class III Antiarrhythmic Agents". *J. Cardiovasc. Cardiol.,* 20 (Suppl. 2):S17-S22). Amiodarone has been shown to possess interesting Class III properties (Singh B. N., Vaughan Williams E. M. "A Third Class Of Anti-Arrhythmic Action Effects On Atrial And Ventricular Intracellular Potentials And Other Pharmacological Actions On Cardiac Muscle, of MJ 1999 and AH 3747" *Br. J. Pharmacol.,* 39:675-689, 1970; Singh B. N., Vaughan Williams E. M, "The Effect Of Amiodarone, A New Anti-Anginal Drug, On Cardiac Muscle", *Br. J. Pharmacol.*, 39:657-667, 1970), although it is not a selective Class III agent because it effects multiple ion channels; additionally, its use is severely limited due to its side effect profile (Nademanee, K. "The Amiodarone Odyssey". *J. Am. Coll. Cardiol.*, 20:1063-1065, 1992; Fuster et al, *Circulation*, 104: 2118-2150, 2001; Bril, A. *Curr. Opin. Pharmacol.* 2:154-159, 2002). Thus, currently available agents such as amiodarone and Class III drugs confer a significant risk of adverse effects including the development of potentially lethal ventricular proarrhythmia.

The ultrarapid delayed rectifier $K^+$ current, $I_{Kur}$, has been observed specifically in human atrium and not in ventricle. The molecular correlate of $I_{Kur}$ in the human atrium is the potassium channel designated Kv1.5. Kv1.5 mRNA (Bertaso, Sharpe, Hendry, and James, *Basic Res. Cardiol.*, 97:424-433, 2002) and protein (Mays, Foose, Philipson, and Tamkun, *J. Clin. Invest.*, 96:282-292, 1995) has been detected in human atrial tissue. In intact human atrial myocytes, an ultra-rapidly activating delayed rectifier $K^+$ current ($I_{Kur}$), also known as the sustained outward current, $I_{sus}$, or $I_{so}$, has been identified and this current has properties and kinetics identical to those expressed by the human $K^+$ channel clone (hKv1.5, HK2) [Wang, Fermini and Nattel, *Circ. Res.*, 73:1061-1076, 1993; Fedida et al., *Circ. Res.* 73:210-216, 1993; Snyders, Tamkun and Bennett, *J. Gen. Physiol.*, 101: 513-543, 1993] and a similar clone from rat brain (Swanson et al., Neuron, 4:929-939, 1990). Furthermore, because of its rapidity of activation and limited slow inactivation, $I_{Kur}$ is believed to contribute significantly to repolarization in human atrium. Consequently, a specific blocker of $I_{Kur}$, that is a compound which blocks Kv1.5, would overcome the shortcoming of other compounds by prolonging refractoriness through retardation of the repolarization in the human atrium without causing the delays in ventricular repolarization that underlie arrhythmogenic afterdepolarizations and acquired long QT syndrome observed during treatment with current Class III drugs. Kv1.5 blockers exhibiting these properties have been described (Peukert et al, *J. Med. Chem.*, 46:486-498, 2003; Knobloch et al, *Naunyn-Schmedieberg's Arch. Pharmacol.* 366:482-287, 2002; Merck & Co., Inc. WO0224655, 2002).

The compounds described in this invention represent a novel structural class of Kv1.5 antagonist.

SUMMARY OF THE INVENTION

This invention relates to potassium channel inhibitors of general structural Formula I

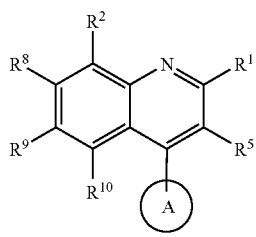

The compounds of this invention are useful in the treatment and prevention of cardiac arrhythmias, and the like. Also within the scope of this invention are pharmaceutical formulations comprising a compound of Formula I and a pharmaceutical carrier.

DETAILED DESCRIPTION OF THE DISCLOSURE

The invention is a compound of formula I

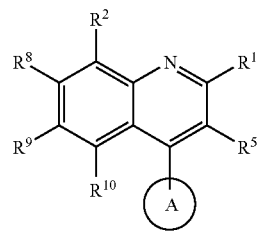

or a pharmaceutically acceptable salt thereof, wherein

A is
a) an aryl ring, wherein any stable aryl ring atom is independently unsubstituted or substituted with
  1) halogen,
  2) $NO_2$,
  3) CN,
  4) $CR^{46}=C(R^{47}R^{48})_2$,
  5) $C\equiv CR^{46}$,
  6) $(CR^iR^j)_rOR^{46}$,
  7) $(CR^iR^j)_rN(R^{46}R^{47})$,
  8) $(CR^iR^j)_rC(O)R^{46}$,
  9) $(CR^iR^j)_rC(O)OR^{46}$,
  10) $(CR^iR^j)_rR^{46}$,
  11) $(CR^iR^j)_rS(O)_{0-2}R^{61}$,
  12) $(CR^iR^j)_rS(O)_{0-2}N(R^{46}R^{47})$,
  13) $OS(O)_{0-2}R^{61}$,
  14) $N(R^{46})C(O)R^{47}$,
  15) $N(R^{46})S(O)_{0-2}R^{61}$,
  16) $(CR^iR^j)_rN(R^{46})R^{61}$,
  17) $(CR^iR^j)_rN(R^{46})R^{61}OR^{47}$,
  18) $(CR^iR^j)_rN(R^{46})(CR^kR^j)_sC(O)N(R^{47}R^{48})$,
  19) $N(R^{46})(CR^iR^j)_rR^{61}$,
  20) $N(R^{46})(CR^iR^j)_rN(R^{47}R^{48})$,
  21) $(CR^iR^j)_rC(O)N(R^{47}R^{48})$, or
  22) oxo, or
b) a heteroaryl ring selected from the group consisting of
  a 5-membered unsaturated monocyclic ring with 1, 2, 3 or 4 heteroatom ring atoms selected from the group consisting or N, O or S,
  a 6-membered unsaturated monocyclic ring with 1, 2, 3 or 4 heteroatom ring atoms selected from the group consisting N, O and S, and
  a 9- or 10-membered unsaturated bicyclic ring with 1, 2, 3 or 4 heteroatom ring atoms selected from the group consisting or N, O or S;
  wherein any stable S heteroaryl ring atom is unsubstituted or mono- or di-substituted with oxo, and any stable C or N heteroaryl ring atom is independently unsubstituted or substituted with
  1) halogen,
  2) $NO_2$,
  3) CN,
  4) $CR^{46}=C(R^{47}R^{48})_2$,
  5) $C\equiv CR^{46}$,
  6) $(CR^iR^j)_rOR^{46}$,
  7) $(CR^iR^j)_rN(R^{46}R^{47})$,
  8) $(CR^iR^j)_rC(O)R^{46}$,
  9) $(CR^iR^j)_rC(O)OR^{46}$, 10) $(CR^iR^j)_rR^{46}$,
11) $(CR^iR^j)_rS(O)_{0-2}R^{61}$,
12) $(CR^iR^j)_rS(O)_{0-2}N(R^{46}R^{47})$,
13) $OS(O)_{0-2}R^{61}$,
14) $N(R^{46})C(O)R^{47}$,
15) $N(R^{46})S(O)_{0-2}R^{61}$,
16) $(CR^iR^j)_rN(R^{46})R^{61}$,
17) $(CR^iR^j)_rN(R^{46})R^{61}OR^{47}$,
18) $(CR^iR^j)_rN(R^{46})(CR^kR^l)_sC(O)N(R^{47}R^{48})$,
19) $N(R^{46})(CR^iR^j)_rR^{61}$,
20) $N(R^{46})(CR^iR^j)_rN(R^{47}R^{48})$,
21) $(CR^iR^j)_rC(O)N(R^{47}R^{48})$, or
22) oxo;

Y is $CH_2$, $NR^{53}$, $NC(O)R^{53}$, $S(O)_{0-2}$ or O;

G is $H_2$ or O;

$R^a$, $R^b$, $R^c$, $R^d$, $R^e$, $R^f$, $R^g$, $R^h$, $R^i$, $R^j$, $R^k$, and $R^l$ are independently selected from the group consisting of:
 1) hydrogen,
 2) $C_1$-$C_6$ alkyl,
 3) halogen,
 4) aryl,
 5) $R^{80}$,
 6) $C_3$-$C_{10}$ cycloalkyl, and
 7) $OR^4$, said alkyl, aryl, and cycloalkyl being unsubstituted, monosubstituted with $R^7$, disubstituted with $R^7$ and $R^{15}$, trisubstituted with $R^7$, $R^{15}$ and $R^{16}$, or tetrasubstituted with $R^7$, $R^{15}$, $R^{16}$ and $R^{17}$;

$R^1$ is independently selected from:
 1) hydrogen,
 2) halogen,
 3) $NO_2$,
 4) CN,
 5) $CR^{40}=C(R^{41}R^{42})$,
 6) $C\equiv CR^{40}$,
 7) $(CR^aR^b)_nOR^{40}$,
 8) $(CR^aR^b)_nN(R^{40}R^{41})$,
 9) $(CR^aR^b)_nC(O)R^{40}$,
 10) $(CR^aR^b)_nC(O)OR^{40}$,
 11) $(CR^aR^b)_nR^{40}$,
 12) $(CR^aR^b)_nS(O)_{0-2}R^6$,
 13) $(CR^aR^b)_nS(O)_{0-2}N(R^{40}R^{41})$,
 14) $OS(O)_{0-2}R^6$,
 15) $N(R^{40})C(O)R^{41}$,
 16) $N(R^{40})S(O)_{0-2}R^6$,
 17) $(CR^aR^b)_nN(R^{40})R^6$,
 18) $(CR^aR^b)_nN(R^{40})R^6OR^{41}$,
 19) $(CR^aR^b)_nN(R^{40})(CR^cR^d)_tC(O)N(R^{41}R^{42})$,
 20) $N(R^{40})(CR^aR^b)_nR^6$,
 21) $N(R^{40})(CR^aR^b)_nN(R^{41}R^{42})$,

22)

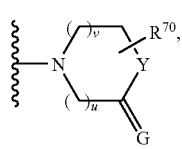

23)

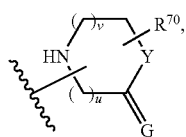

24)

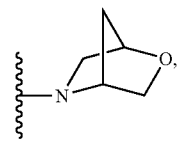

25) $(CR^aR^b)_nC(O)N(R^{41}R^{42})$, and
26) a 4-, 5-, or 6-membered heterocyclic ring containing 1 nitrogen atom, unsubstituted, or mono, di- or tri-substituted with —OH;

$R^2$, $R^8$, $R^9$ and $R^{10}$ are independently selected from:
 1) hydrogen,
 2) halogen,
 3) $NO_2$,
 4) CN,
 5) $CR^{43}=C(R^{44}R^{45})$,
 6) $C\equiv CR^{43}$,
 7) $(CR^eR^f)_pOR^{43}$,
 8) $(CR^eR^f)_pN(R^{43}R^{44})$,
 9) $(CR^eR^f)_pC(O)R^{43}$,
 10) $(CR^eR^f)_pC(O)OR^{43}$,
 11) $(CR^eR^f)_pR^{43}$,
 12) $(CR^eR^f)_pS(O)_{0-2}R^{60}$,
 13) $(CR^eR^f)_pS(O)_{0-2}N(R^{43}R^{44})$,
 14) $OS(O)_{0-2}R^{60}$,
 15) $N(R^{43})C(O)R^{44}$,
 16) $N(R^{43})S(O)_{0-2}R^{60}$,
 17) $(CR^eR^f)_pN(R^{43})R^{60}$,
 18) $(CR^eR^f)_pN(R^{43})R^{60}OR^{44}$,
 19) $(CR^eR^f)_pN(R^{43})(CR^gR^h)_qC(O)N(R^{44}R^{45})$,
 20) $N(R^{43})(CR^eR^f)_pR^{60}$,
 21) $N(R^{43})(CR^eR^f)_pN(R^{44}R^{45})$, and
 22) $(CR^eR^f)_pC(O)N(R^{43}R^{44})$, or $R^2$ and $R^8$ are independently as defined above, and $R^9$ and $R^{10}$, together with the atoms to which they are attached, form the ring

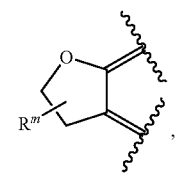

where $R^m$ is $C_{1-6}$alkyl;

$R^4$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, and $R^{53}$ are independently selected from:
 1) hydrogen,
 2) $C_1$-$C_6$ alkyl,
 3) $C_3$-$C_{10}$ cycloalkyl,
 4) aryl, 5) $R^{81}$,
6) $CF_3$,
7) $C_2$-$C_6$ alkenyl, and
8) $C_2$-$C_6$ alkynyl, said alkyl, aryl, and cycloalkyl is unsubstituted, mono-substituted with $R^{18}$, di-substituted with $R^{18}$ and $R^{19}$, tri-substituted with $R^{18}$, $R^{19}$ and $R^{20}$, or tetra-substituted with $R^{18}$, $R^{19}$, $R^{20}$ and $R^{21}$;

$R^5$ is independently selected from:
1) hydrogen,
2) halogen,
3) CN,
4) $C(O)N(R^{49}R^{50})$,
5) $C(O)OR^{49}$,
6) $S(O)_{0-2}N(R^{49}R^{50})$,
7) $S(O)_{0-2}R^{62}$,
8) $C_1$-$C_6$ alkyl,
9) $C_3$-$C_{10}$ cycloalkyl,
10) $R^{82}$, said alkyl, aryl, and cycloalkyl is unsubstituted, mono-substituted with $R^{22}$, di-substituted with $R^{22}$ and $R^{23}$, tri-substituted with $R^{22}$, $R^{23}$ and $R^{24}$, or tetra-substituted with $R^{22}$, $R^{23}$, $R^{24}$ and $R^{25}$;

$R^6$, $R^{60}$, $R^{61}$, $R^{62}$ and $R^{63}$ are independently selected from:
1) $C_1$-$C_6$ alkyl,
2) aryl,
3) $R^{83}$, and
4) $C_3$-$C_{10}$ cycloalkyl;

said alkyl, aryl, and cycloalkyl is unsubstituted, mono-substituted with $R^{26}$, di-substituted with $R^{26}$ and $R^{27}$, tri-substituted with $R^{26}$, $R^{27}$ and $R^{28}$, or tetra-substituted with $R^{26}$, $R^{27}$, $R^{28}$ and $R^{29}$;

$R^7$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{70}$ are independently selected from:
1) $C_1$-$C_6$ alkyl,
2) halogen,
3) $OR^{51}$,
4) $CF_3$,
5) aryl,
6) $C_3$-$C_{10}$ cycloalkyl,
7) $R^{84}$,
8) $S(O)_{0-2}N(R^{51}R^{52})$,
9) $C(O)OR^{51}$,
10) $C(O)R^{51}$,
11) CN,
12) $C(O)N(R^{51}R^{52})$,
13) $N(R^{51})C(O)R^{52}$,
14) $S(O)_{0-2}R^{63}$,
15) $NO_2$, and
16) $N(R^{51}R^{52})$;

$R^{80}$, $R^{81}$, $R^{82}$, $R^{83}$ and $R^{84}$ are independently selected from a group of unsubstituted or substituted heterocyclic rings consisting of a 4-6 membered unsaturated or saturated monocyclic ring with 1, 2, 3 or 4 heteroatom ring atoms selected from the group consisting N, O and S, and a 9- or 10-membered unsaturated or saturated bicyclic ring with 1, 2, 3 or 4 heteroatom ring atoms selected from the group consisting or N, O or S;

n, p, q, r, s and t are independently 0, 1, 2, 3, 4, 5 or 6;

u is 0, 1 or 2; and v is 0, 1 or 2.

In a class of compounds of the invention, or pharmaceutically acceptable salts thereof, A is an aryl ring selected from phenyl, unsubstituted or substituted as defined above, or a heteroaryl ring, unsubstituted or substituted as defined above, selected from the group consisting of pyridine, pyrimidine, pyrazine, pyridazine, indole, pyrrolopyridine, benzimidazole, benzoxazole, benzothiazole, and benzoxadiazole;

$R^2$, $R^8$, $R^9$ and $R^{10}$ are independently selected from the group consisting of:
1) hydrogen,
2) halogen,
3) $OR^{43}$, and
4) $(CR^eR^f)_pR^{43}$,
or $R^2$ and $R^8$ are independently as defined above, and $R^9$ and $R^{10}$, together with the atoms to which they are attached, form the ring

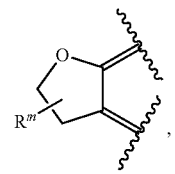

where $R^m$ is $C_{1-6}$alkyl; and $R^1$ is independently selected from:
1) hydrogen,
2) halogen,
3) CN,
4) $OR^{40}$,
5) $N(R^{40}R^{41})$,
6) $C(O)OR^{40}$,
7) $R^{81}$,
8) $S(O)_{0-2}R^6$,
9) $N(R^{40})(CR^aR^b)_nR^6$, wherein $R^6=R^{83}$,
10) $N(R^{40})(CR^aR^b)_nN(R^{41}R^{42})$,

11)

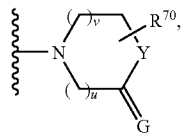

12)

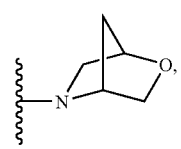

13) $C(O)N(R^{41}R^{42})$, and
14) a 4-, 5-, or 6-membered heterocyclic ring containing 1 nitrogen atom, unsubstituted, or mono-, di- or tri-substituted with —OH.

In a subclass of this class of compounds of the invention, or pharmaceutically acceptable salts thereof, $R^2$, $R^8$ and $R^{10}$ are hydrogen, and $R^9$ is $OR^{43}$.

In a group of the subclass of compounds, or pharmaceutically acceptable salts thereof, $R^1$ is selected from the group consisting of Cl, $OR^{40}$, and $NHR^{40}$.

In a subgroup of the group of compounds, or pharmaceutically acceptable salts thereof, A is an aryl ring, unsubstituted or substituted with halogen.

In a family of the subgroup of compounds, or pharmaceutically acceptable salts thereof, $R^5$ is CN.

In a subfamily of the family of compounds, or pharmaceutically acceptable salts thereof, A is fluorophenyl or chlorophenyl;

$R^1$ is selected from the group consisting of

—OCH$_2$CHCH$_2$, —OCH$_2$CH(OH)CH$_2$OH, —O(CH$_2$)$_3$CHCH$_2$, OCH$_3$, —O(CH$_2$)$_3$CH(OH)CH$_2$OH, Cl, —NHCH$_2$CH$_2$OH, —NHCH$_2$CH(OH)CH$_2$OH, —NHCH$_2$CH(OH)CH$_2$OH,

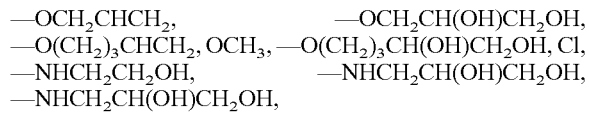

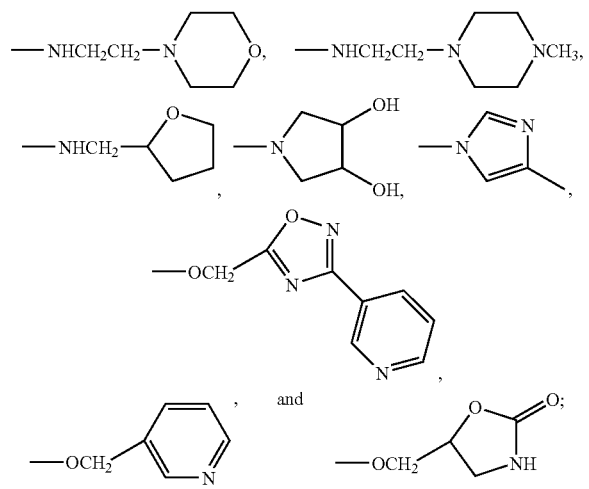

and $R^9$ is —OCH$_3$.

A preferred embodiment is a compound selected from the group consisting of 2-(Allyloxy)-4-(3-fluorophenyl)-6-methoxyquinoline-3-carbonitrile, (±)-2-2,3-Dihydroxypropoxy)-4-(3-fluorophenyl)-6-methoxyquinoline-3-carbonitrile, 4-(3-Fluorophenyl)-6-methoxy-2-[(3-pyridin-3-yl-1,2,4-oxadiazol-5-yl)methoxy]quinoline-3-carbonitrile, 4-(3-Fluorophenyl)-6-methoxy-2-[(3-pyridin-3-yl)methoxy]quinoline-3-carbonitrile, (±)-4-(3-Fluorophenyl)-6-methoxy-2-[(2-oxo-1,3-oxazolidin-5-yl)methoxy]quinoline-3-carbonitrile, 4-(3-Fluorophenyl)-6-methoxy-2-(pent-4-enyloxy)quinoline-3-carbonitrile, (±)-2-[(4,5-Dihydroxypentyl)oxy]-4-(3-fluorophenyl)-6-methoxyquinoline-3-carbonitrile, 2-Chloro-4-(3-fluorophenyl)-6-methoxyquinoline-3-carbonitrile, 2-Chloro-4-(3-chlorophenyl)-6-methoxyquinoline-3-carbonitrile, (2S)-2-[(2,3-Dihydroxypropyl)amino]-4-(3-fluorophenyl)-6-methoxyquinoline-3-carbonitrile, (2R)-2-[(2,3-Dihydroxypropyl)amino]-4-(3-fluorophenyl)-6-methoxyquinoline-3-carbonitrile, (3R,4R)-2-(3,4-Dihydroxypyrrolidin-1-yl)-4-(3-fluorophenyl)-6-methoxyquinoline-3-carbonitrile, (3S,4S)-2-(3,4-Dihydroxypyrrolidin-1-yl)-4-(3-fluorophenyl)-6-methoxyquinoline-3-carbonitrile, 4-(3-fluorophenyl)-6-methoxy-2-(4-methyl-1H-imidazol-1-yl)quinoline-3-carbonitrile, 2-(2-(N-morpholinyl)ethylamino)-6-methoxy-4-(3-fluorophenyl)quinoline-3-carbonitrile, 2-(2-(4-methylpiperidin-1-yl)ethylamino)-6-methoxy-4-(3-fluorophenyl)quinoline-3-carbonitrile, 2-(2-hydroxyethylamino)-6-methoxy-4-(3-chlorophenyl)quinoline-3-carbonitrile, and 2-(tetrahydrofuranyl methylamino)-6-methoxy-4-(3-chlorophenyl)quinoline-3-carbonitrile.

2-Allyloxy)-4-(3-fluorophenyl)-6-methoxyquinoline-3-carbonitrile, (±)-2-(2,3-Dihydroxypropoxy)-4-(3-fluorophenyl)-6-methoxyquinoline-3-carbonitrile, 4-(3-Fluorophenyl)-6-methoxy-2-[(3-pyridin-3-yl-1,2,4-oxadiazol-5-yl)methoxy]quinoline-3-carbonitrile, 4-(3-Fluorophenyl)-6-methoxy-2-[(3-pyridin-3-yl)methoxy]quinoline-3-carbonitrile, (±)-4-(3-Fluorophenyl)-6-methoxy-2-[(2-oxo-1,3-oxazolidin-5-yl)methoxy]quinoline-3-carbonitrile, 4-(3-Fluorophenyl)-6-methoxy-2-(pent-4-enyloxy)quinoline-3-carbonitrile, (±)-2-[(4,5-Dihydroxypentyl)oxy]-4-(3-fluorophenyl)-6-methoxyquinoline-3-carbonitrile, 2-Chloro-4-(3-fluorophenyl)-6-methoxyquinoline-3-carbonitrile, (2S)-2-[(2,3-Dihydroxypropyl)amino]-4-3-fluorophenyl)-6-methoxyquinoline-3-carbonitrile, (2R)-2-[(2,3-Dihydroxypropyl)amino]-4-(3-fluorophenyl)-6-methoxyquinoline-3-carbonitrile, (3R,4R)-2-(3,4-Dihydroxypyrrolidin-1-yl)-4-(3-fluorophenyl)-6-methoxyquinoline-3-carbonitrile, (3S,4S)-2-(3,4-Dihydroxypyrrolidin-1-yl)-4-3-fluorophenyl)-6-methoxyquinoline-3-carbonitrile, and 4-(3-fluorophenyl)-6-methoxy-2-(4-methyl-1H-imidazol-1-yl)quinoline-3-carbonitrile, or a pharmaceutically acceptable salt thereof.

The above-listed compounds are active in one or more of the assays for Kv1.5 described below.

Another embodiment of the invention is a method of treating or preventing a condition in a mammal, the treatment or prevention of which is effected or facilitated by $K_v1.5$ inhibition, which comprises administering an amount of a compound of Formula I that is effective at inhibiting $K_v1.5$.

A preferred embodiment is a method of treating or preventing cardiac arrhythmias, e.g. atrial fibrillation, atrial flutter, atrial arrhythmia, and supraventricular tachycardia, in a mammal, which comprises administering a therapeutically effective amount of a compound of Formula I. Another preferred embodiment is a method of preventing thromboembolic events, such as stroke. Another preferred embodiment is a method of preventing congestive heart failure. Another preferred embodiment is a method of treating or preventing immunodepression or a disorder involving immunodepression, such as AIDS, cancer, senile dementia, trauma (including wound healing, surgery and shock) chronic bacterial infection, certain central nervous system disorders, and conditions including resistance by transplantation of organs or tissue, graft-versus-host diseases brought about by medulla ossium transplantation. Within this embodiment is a method for treating or preventing immunodepression by administering a compound of the invention with an immunosuppresant compound. Another preferred embodiment is a method of treating or preventing gliomas including those of lower and higher malignancy, preferably those of higher malignancy. Another preferred embodiment is a method for inducing in a patient having atrial fibrillation, a condition of normal sinus rhythm, in which the induced rhythm corresponds to the rhythm that would be considered normal for an individual sharing with the patient similar size and age characteristics, which comprises treating the patient with a compound of the invention. Another preferred embodiment is a method for treating tachycardia, (i.e., rapid heart rate e.g. 100 beats per minute) in a patient which comprises treating the patient with an antitachycardia device (e.g. a defibrillator or a pacemaker) in combination with a compound of the invention.

The present invention also encompasses a pharmaceutical formulation comprising a pharmaceutically acceptable carrier and the compound of Formula I or a pharmaceutically acceptable crystal form or hydrate thereof. A preferred embodiment is a pharmaceutical composition of the compound of Formula I, comprising, in addition, a second agent.

The compounds of the present invention may have asymmetric centers or asymmetric axes, and this invention includes all of the optical isomers and mixtures thereof. Unless specifically mentioned otherwise, reference to one isomer applies to both isomers.

In addition compounds with carbon-carbon double bonds may occur in Z- and E-forms with all isomeric forms of the compounds being included in the present invention.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. The term "alkoxy" represents a linear or branched alkyl group of indicated number of carbon atoms attached through an oxygen bridge. The term "alkylene" refers to a divalent hydrocarbon radical having a specified number of carbon atoms, e.g. $C_3$ alkylene is propylene moiety represented by —$CH_2CH_2CH_2$—.

The term "alkenyl" includes both branched and straight chain unsaturated hydrocarbon groups containing at least two carbon atoms joined by a double bond. The alkene ethylene is represented, for example, by "$CH_2CH_2$" or alternatively, by "$H_2C$=$CH_2$". "$C_{2-5}$ alkenyl" (or "$C_2$-$C_5$ alkenyl") for example, means linear or branched chain alkenyl groups having from 2 to 5 carbon atoms and includes all of the pentenyl isomers as well as 1-butenyl, 2-butenyl, 3-butenyl, 1-propenyl, 2-propenyl, and ethenyl (or ethylenyl). Similar terms such as "$C_{2-3}$ alkenyl" have an analogous meaning.

The term "alkynyl" includes both branched and straight chain unsaturated hydrocarbon groups containing at least two carbon atoms joined by a triple bond. The alkyne acetylene is represented, for example, by "CHCH" or alternatively, by "HC≡CH". "$C_{2-5}$ alkynyl" (or "$C_2$-$C_5$ alkynyl") for example, means linear or branched chain alkynyl groups having from 2 to 5 carbon atoms and includes all of the pentynyl isomers as well as 1-butynyl, 2-butynyl, 3-butynyl, 1-propy-nyl, 2-propynyl, and ethynyl (or acetylenyl). Similar terms such as "$C_{2-3}$ alkynyl" have an analogous meaning.

Unless otherwise noted, alkyl, alkoxy, alkenyl, alkynyl and alkylene groups are unsubstituted or substituted with 1 to 3 substituents on each carbon atom, with halo, $C_1$-$C_{20}$ alkyl, $CF_3$, $NH_2$, $N(C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2N$—C(NH)—, —O($C_1$-$C_6$ alkyl)$CF_3$, ($C_0$-$C_6$ alkyl)C(O)—, ($C_0$-$C_6$ alkyl) OC(O)—, ($C_0$-$C_6$ alkyl)O($C_1$-$C_6$ alkyl)-, ($C_0$-$C_6$ alkyl) C(O)$_{1-2}$($C_0$-$C_6$ alkyl)-, ($C_0$-$C_6$ alkyl)OC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocy-clylalkyl.

The term "$C_0$" as employed in expressions such as "$C_{0-6}$ alkyl" means a direct covalent bond. Similarly, when an integer defining the presence of a certain number of atoms in a group is equal to zero, it means that the atoms adjacent thereto are connected directly by a bond. For example, in the structure

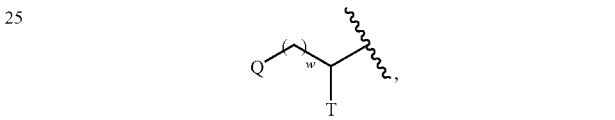

wherein w is an integer equal to zero, 1 or 2, the structure is

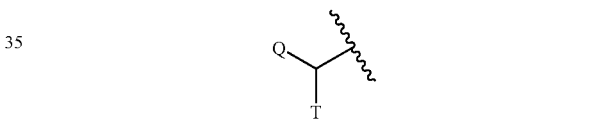

when w is zero.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "$C_{1-6}$ haloalkyl" (which may alternatively be referred to as "$C_1$-$C_6$ haloalkyl" or "halogenated $C_1$-$C_6$ alkyl") means a $C_1$ to $C_6$ linear or branched alkyl group as defined above with one or more halogen substituents. The term "$C_{1-4}$ haloalkyl" has an analogous meaning. The term "$C_{1-6}$ fluoroalkyl" has an analogous meaning except that the halogen substituents are restricted to fluoro. Suitable fluoro-alkyls include the series ($CH_2$)$_{0-4}$$CF_3$ (i.e., trifluoromethyl, 2,2,2-trifluoroethyl, 3,3,3-trifluoro-n-propyl, etc.).

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

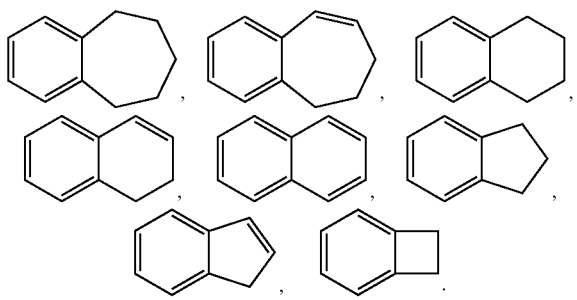

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, and biphenylenyl.

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. The heterocyclic ring may be attached at any heteroatom or carbon atom, provided that attachment results in the creation of a stable structure. When the heterocyclic ring has substituents, it is understood that the substituents may be attached to any atom in the ring, whether a heteroatom or a carbon atom, provided that a stable chemical structure results.

As used herein, the terms "substituted $C_3$-$C_{10}$ cycloalkyl", "substituted aryl" and "substituted heterocycle" are intended to include the cyclic group containing from 1 to 3 substituents in addition to the point of attachment to the rest of the compound. Preferably, the substituents are selected from the group which includes, but is not limited to, halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2N$—C(NH)—, —O($C_1$-$C_6$ alkyl)$CF_3$, ($C_0$-$C_6$ alkyl)C(O)—, ($C_0$-$C_6$ alkyl) OC(O)—, ($C_0$-$C_6$alkyl)O($C_1$-$C_6$ alkyl)-, ($C_0$-$C_6$ alkyl) C(O)$_{1-2}$($C_0$-$C_6$ alkyl)-, ($C_0$-$C_6$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4 to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic ring which consists of carbon atoms and one or more heteroatoms selected from N, O and S. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e.,

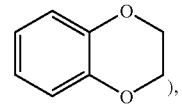), imidazo(2,1-b)(1,3)thiazole, (i.e.,

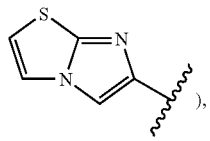), and benzo-1,3-dioxolyl (i.e.,

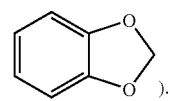).

In certain contexts herein,

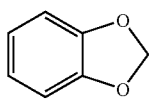

is alternatively referred to as phenyl having as a substituent methylenedioxy attached to two adjacent carbon atoms.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

In compounds of the invention having pyridyl N-oxide moieties, the pyridyl-N-oxide portion is structurally depicted using conventional representations such as

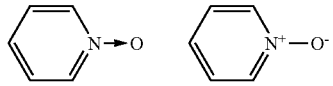

which have equivalent meanings.

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

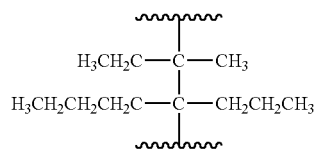

Pharmaceutically acceptable salts include both the metallic (inorganic) salts and organic salts; a list of which is given in *Remington's Pharmaceutical Sciences,* 17th Edition, pg. 1418 (1985). It is well known to one skilled in the art that an appropriate salt form is chosen based on physical and chemical stability, flowability, hydro-scopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I.

Methods for preparing the compounds of this invention are illustrated in the following schemes. All variables are as defined above unless otherwise specified. Other synthetic protocols will be readily apparent to those skilled in the art.

Scheme 1

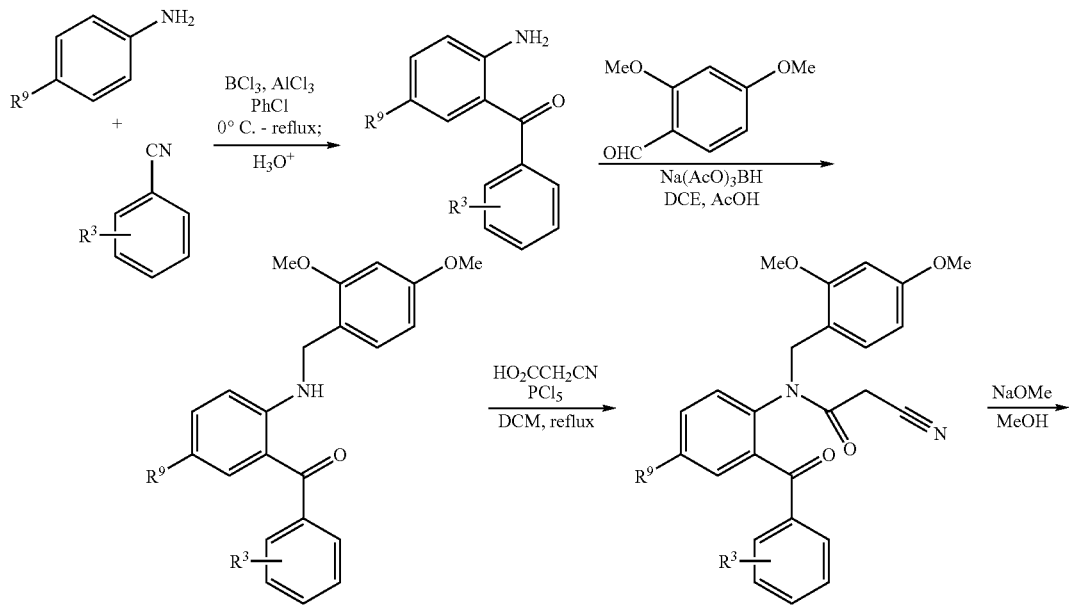

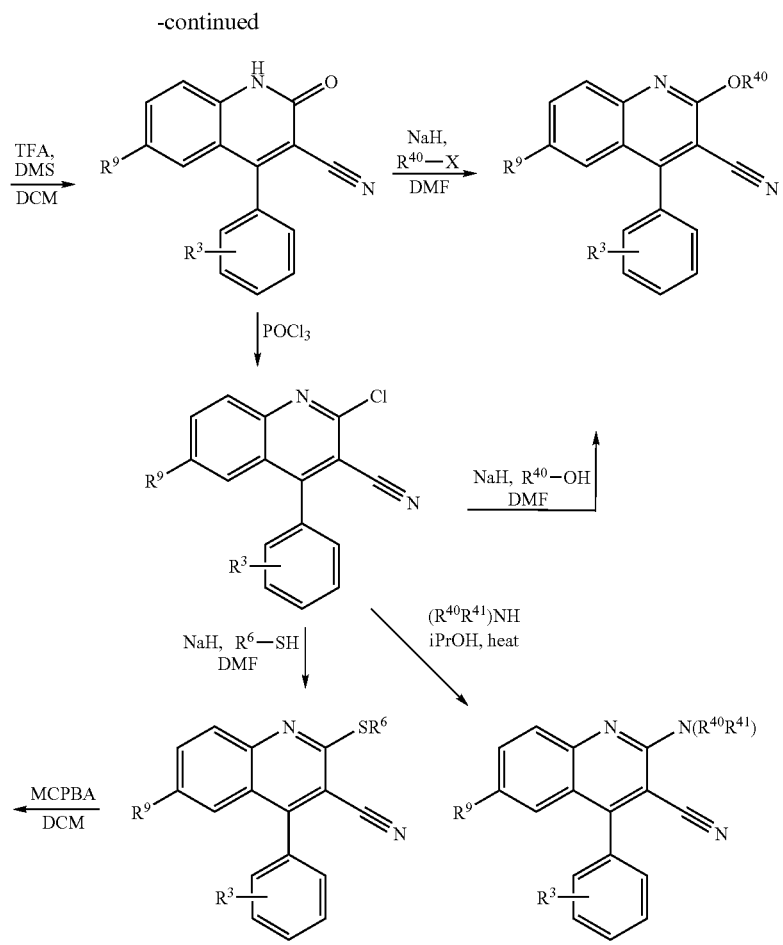

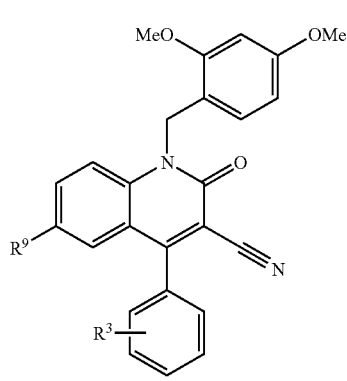

R[3] is Cl or F

The following examples illustrate the preparation of the compounds of Formula I and as such are not to be considered as limiting the invention set forth in the claims appended hereto. Examples provided are intended to assist in a further understanding of the invention. Particular materials employed, species and conditions are intended to be further illustrative of the invention and not limiting of the reasonable scope thereof. In all cases, the proton NMR for each product was consistent with that of the structure shown.

Example 1

2-(Allyloxy)-4-(3-fluorophenyl)-6-methoxyquinoline-3-carbonitrile

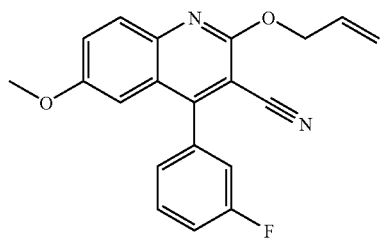

Step A:
(2-Amino-5-methoxyphenyl)(3-fluorophenyl)methanone

To a 0° C. solution of para-anisidine (8.13 g, 66.0 mmol) in 25 mL of chlorobenzene was added dropwise a solution of $BCl_3$ in dichloromethane (74.3 mL of 1 M, 74.3 mmol). The mixture was stirred at room temperature for one hour, then transferred slowly via syringe to solution of 3-fluorobenzonitrile (4.00 g, 33.0 mmol) and $AlCl_3$ (5.06 g, 37.9 mmol) in 50 mL of chlorobenzene at 60° C. After the addition was complete, the reaction was stirred at 70° C. for 3 hours, then cooled to room temperature and stirred overnight. Water was added (125 mL), and the mixture stirred at 85 degrees for 6 hours. After cooling to room temperature, the mixture was poured into water, and the organic layer was extracted with saturated $NaHCO_3$ solution and brine, dried over $Na_2SO_4$, filtered, and concentrated in vacuo. The crude residue was purified by flash chomatography through $SiO_2$ (50-100% $CH_2Cl_2$/hexane) to provide the titled product (1.83 g, 23% yield) as a red oil. Proton NMR for the product was consistent with the titled compound. HRMS (ES) exact mass calculated for $C_{14}H_{13}FNO_2$ (M+H$^+$): 246.0929. Found 246.0925.

Step B: {2-[(2,4-Dimethoxybenzyl)amino]-5-methoxyphenyl}(3-fluorophenyl)methanone To a solution of (2-Amino-5-methoxyphenyl)(3-fluorophenyl)methanone (0.984 g, 4.01 mmol) in 15 mL of dichloroethane was added 4 Å powdered molecular sieves (1 g), followed by sodium triacetoxyborohydride (2.55 g, 12.0 mmol) and acetic acid (0.69 mL, 12.0 mmol). 2,4-Dimethoxybenzaldehyde was added (0.667 g, 4.01 mmol), and the reaction was stirred at room temperature for 3 hours. The reaction was partitioned between EtOAc and saturated NaHCO$_3$ solution, and the organic layer was washed with brine, dried over Na$_2$SO$_4$, filtered, and concentrated in vacuo. The titled product was isolated as a red oil (1.66 g) which was used in the next step without further purification. ESI+ MS: 396.2 [M+H]$^+$.

Step C: 2-Cyano-N-(2,4-dimethoxybenzyl)-N-[2-(3-fluorobenzoyl)-4-methoxyphenyl]acetamide To a solution of cyanoacetic acid (43.0 mg, 0.511 mmol) in 1 mL of dichloromethane at room temperature was added PCl$_5$ (106 mg, 0.511 mmol). The mixture was heated to reflux for 10 minutes. A solution of {2-[(2,4-dimethoxybenzyl)amino]-5-methoxyphenyl}(3-fluorophenyl)methanone (101 mg, 0.255 mmol) in 1 mL dichloromethane was added, and the reaction was refluxed for an additional 1.5 hours. The reaction was partitioned between EtOAc and saturated NaHCO$_3$ solution, and the organic layer was washed with brine, dried over Na$_2$SO$_4$, filtered, and concentrated in vacuo. The titled product was isolated as a yellow foam (117 mg, 99% yield) which was used in the next step without further purification. Proton NMR for the product was consistent with the titled compound. ESI+ MS: 463.2 [M+H]$^+$.

Step D: 1-(2,4-Dimethoxybenzyl)-4(3-fluorophenyl)-6-methoxy-2-oxo-1,2-dihydroquinoline-3-carbonitrile To solution of 2-cyano-N-(2,4-dimethoxybenzyl)-N-[2-(3-fluorobenzoyl)-4-methoxyphenyl]acetamide (56.0 mg, 0.121 mmol) in 1 mL of methanol was added sodium methoxide solution in methanol (0.083 mL of 4.37 M, 0.363 mmol). The solution was heated to reflux for 5 minutes, then cooled to room temperature. The reaction was partitioned between EtOAc and water, and the organic layer was washed with brine, dried over Na$_2$SO$_4$, filtered, and concentrated in vacuo. The crude residue was purified by flash chomatography through SiO$_2$ (30-50% EtOAc/hexane) to provide the titled product as a yellow foam. $^1$H-NMR (500 MHz, CDCl$_3$) δ 7.56-7.60 (m, 1H), 7.39 (d, J=9.5 Hz, 1H), 7.25-7.31 (m, 2H), 7.17-7.21 (m, 2H), 6.91 (d, J=8.5 Hz, 1H), 6.74 (br s, 1H), 6.52 (br s, 1H), 6.38 (br d, J=8.5 Hz, 1H), 5.54 (s, 2H), 3.95 (s, 3H), 3.77 (s, 3H), 3.67 (s, 3H) ppm. HRMS (ES) exact mass calculated for C$_{26}$H$_{22}$FN$_2$O$_4$ (M+H$^+$): 445.1558. Found 445.1574.

Step E: 4-(3-Fluorophenyl)-6-methoxy-2-oxo-1,2-dihydroquinoline-3-carbonitrile To a solution of 1-(2,4-dimethoxybenzyl)-4-(3-fluorophenyl)-6-methoxy-2-oxo-1,2-dihydroquinoline-3-carbonitrile (42 mg, 0.094 mmol) in 0.5 mL of dichloromethane and 1 mL of trifluoroacetic acid was added dimethyl sulfide (0.10 mL). After stirring for 2 days, the reaction was heated to reflux for 10 hours, then concentrated in vacuo. The crude product was triturated with EtOAc to provide the titled product as a pale yellow solid. Proton NMR for the product was consistent with the titled compound. HRMS (ES) exact mass calculated for C$_{17}$H$_{11}$FN$_2$O$_2$ (M+H$^+$): 295.0878. Found 295.0879.

Step F: 2-(Allyloxy)-4-3-fluorophenyl)-6-methoxyquinoline-3-carbonitrile

To a solution of 4-(3-fluorophenyl)-6-methoxy-2-oxo-1,2-dihydroquinoline-3-carbonitrile (1.00 g, 3.40 mmol) in 20 mL of N,N-dimethylformamide at 0° C. was added sodium hydride (163 mg of 60% dispersion in mineral oil, 4.08 mmol). After 30 minutes, allyl iodide was added (0.342 mL, 3.74 mmol), and the reaction was stirred for 2 hours. The reaction was quenched with water and partitioned between EtOAc and water, and the organic layer was washed with brine, dried over Na$_2$SO$_4$, filtered, and concentrated in vacuo. The crude residue was subjected to flash chomatography through SiO$_2$ (5-60% EtOAc/hexane) to provide the second eluting product as the titled compound. $^1$H NMR, difference nOe, and HMQC NMR spectral data for the product were consistent with the titled compound. ESI+ MS: 335.1 [M+H]$^+$.

Example 2

(±)-2-(2,3-Dihydroxypropoxy)-4-(3-fluorophenyl)-6-methoxyquinoline-3-carbonitrile, enantiomer A

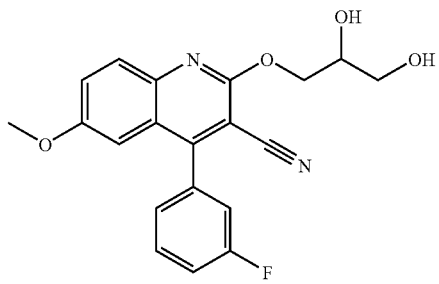

To a solution of 2-(allyloxy)-4-3-fluorophenyl)-6-methoxyquinoline-3-carbonitrile (140 mg, 0.419 mmol) in 10 mL of tBuOH:THF:water (10:3:1) was added N-methylmorpholine N-oxide (49 mg, 0.42 mmol), followed by a solution of OsO4 (106 mg, 0.42 mmol) in water (ca. 0.5 mL). After stirring for 18 hours, the reaction was diluted with EtOAc, washed with saturated NaHCO$_3$ solution, 10% citric acid solution and brine, and the organic layer was dried over Na$_2$SO$_4$, filtered, and concentrated in vacuo. The crude residue (144 mg) was subjected to preparative chiral HPLC through a Chiralcel OD column (85% hexanes containing 0.1% diethylamine:EtOH). The first eluting peak was collected and concentrated in vacuo to provide the titled product. $^1$H-NMR (500 MHz, CDCl$_3$) δ 7.81 (d, J=9.0 Hz, 1H), 7.70 (ddd, J=8.1, 8.1, 5.6 Hz, 1H), 7.44 (dd, J=9.0, 2.9 Hz, 1H), 7.30 (ddd, J=8.6, 2.4, 1.0 Hz, 1H), 7.25 (m, 1H), 7.19 (br d, J=8.6 Hz, 1H), 6.83 (d, J=2.9 Hz, 1H), 4.68-4.76 (m, 2H), 4.19 (m, 1H), 3.84 (dd, J=11.6, 4.1 Hz, 1H), 3.79 (dd, J=11.6, 5.4 Hz, 1H), 3.74 (s, 3H) ppm. HRMS (ES) exact mass calculated for C$_{20}$H$_{18}$FN$_2$O$_4$ (M+H$^+$): 369.1245. Found 369.1195.

Example 3

(±)-2-(2,3-Dihydroxypropoxy)-4-(3-fluorophenyl)-6-methoxyquinoline-3-carbonitrile, enantiomer B

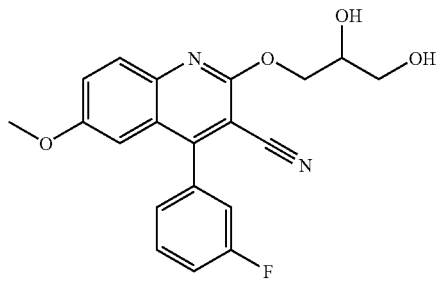

The crude residue from Example 2 was subjected to preparative chiral HPLC through a Chiralcel OJ column (85% hexanes containing 0.1% diethylamine:EtOH). The second eluting peak was collected and concentrated in vacuo to provide the titled product. Proton NMR for the product was consistent with the titled compound. HRMS (ES) exact mass calculated for $C_{20}H_{18}FN_2O_4$ (M+H$^+$): 369.1245. Found 369.1239.

Example 4

4-3-Fluorophenyl)-6-methoxy-2-[(3-pyridin-3-yl-1,2,4-oxadiazol-5-yl)methoxy]quinoline-3-carbonitrile

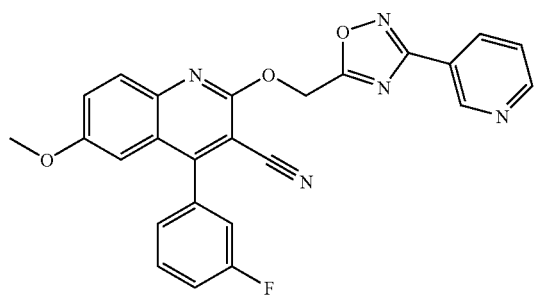

Following the procedure described in Step F of Example 1, replacing allyl iodide with 5-chloromethyl-3-(pyridin-3-yl)-1,2,4-oxadiazole, the titled compound was obtained as the first eluting product after purification by flash chromatography through silica gel (EtOAc:hexane). Proton NMR for the product was consistent with the titled compound. $^1$H NMR, difference nOe, and HMQC NMR spectral data for the product were consistent with the titled compound. HRMS (ES) exact mass calculated for $C_{23}H_{17}FN_5O_3$ (M+H$^+$): 454.1310. Found 454.1313.

Example 5

4-(3-Fluorophenyl)-6-methoxy-2-[(3-pyridin-3-yl)methoxy]quinoline-3-carbonitrile

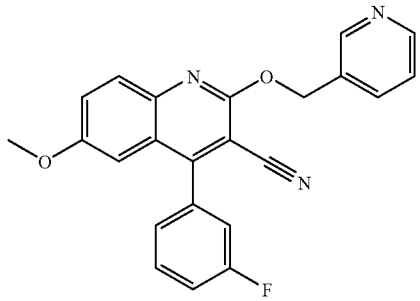

To a solution of 4-(3-fluorophenyl)-6-methoxy-2-oxo-1,2-dihydroquinoline-3-carbonitrile (50.0 mg, 0.170 mmol) in 2 mL of 1,2-dimethoxyethane and 0.5 mL of N,N-dimethylformamide at 0° C. was added sodium hydride (10.0 mg of 60% dispersion in mineral oil, 0.26 mmol). After 10 minutes, lithium bromide was added (30 mg, 0.34 mmol), and the reaction was stirred for one hour. 2-(Chloromethyl)pyridine hydrochloride (33 mg, 0.17 mmol) was added, and the reaction was allowed to warm to room temperature. After 18 hours, another portion of sodium hydride (10.0 mg of 60% dispersion in mineral oil, 0.26 mmol) was added. After 24 hours, the reaction was quenched with water and partitioned between EtOAc and water, and the organic layer was washed with brine, dried over Na$_2$SO$_4$, filtered, and concentrated in vacuo. The titled compound was obtained as the second eluting product after purification by preparative reversed phase HPLC. Proton NMR for the product was consistent with the titled compound. $^1$H NMR, difference nOe, and HMQC NMR spectral data for the product were consistent with the titled compound. HRMS (ES) exact mass calculated for $C_{23}H_{17}FN_3O_2$ (M+H$^+$): 386.1299. Found 386.1303.

Example 6

(±)-4-(3-Fluorophenyl)-6-methoxy-2-[(2-oxo-1,3-oxazolidin-5-yl)methoxy]quinoline-3-carbonitrile

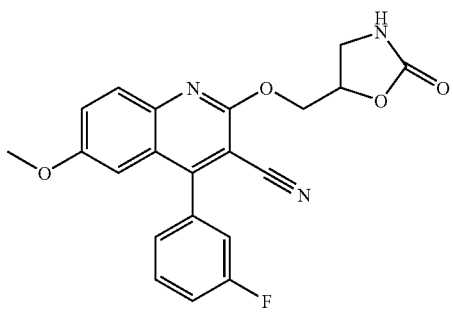

Following the procedure described in Step F of Example 1, replacing allyl iodide with 5-(chloromethyl)-1,3-oxazolidin-2-one, and heating the reaction in a pressure tube at 120° C. for 16 hours, the titled compound was obtained after purification by preparative reversed phase HPLC (first eluting product). $^1$H NMR, difference nOe, COSY, HMBC and

Example 7

4-(3-Fluorophenyl)-6-methoxy-2-(pent-4-enyloxy)quinoline-3-carbonitrile

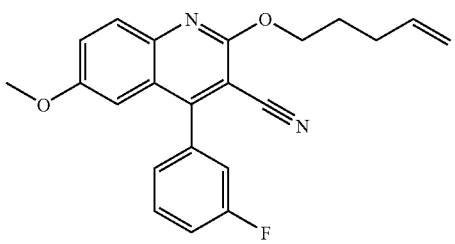

Following the procedure described in Step F of Example 1, replacing allyl iodide with 5-bromopentene, the titled compound was obtained after purification by crystallization from EtOAc/hexane, followed by further purification by preparative reversed phase HPLC (first eluting product). $^1$H NMR, difference nOe, and HMQC NMR spectral data for the product were consistent with the titled compound. HRMS (ES) exact mass calculated for $C_{22}H_{20}FN_2O_2$ (M+H$^+$): 363.1504. Found 363.1500.

Example 8

($\pm$)-2-[(4,5-Dihydroxypentyl)oxy]-4-(3-fluorophenyl)-6-methoxyquinoline-3-carbonitrile

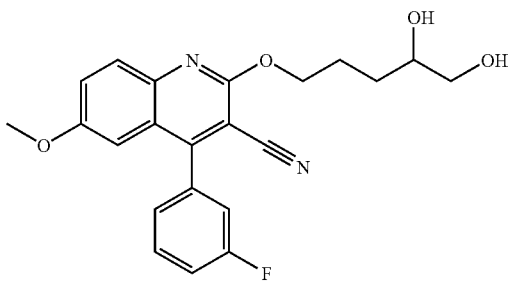

Following the procedure described in Example 2, replacing 2-(allyloxy)-4-(3-fluorophenyl)-6-methoxyquinoline-3-carbonitrile with 4-(3-fluorophenyl)-6-methoxy-2-(pent-4-enyloxy)quinoline-3-carbonitrile, the titled compound was obtained after precipitation of the crude product from EtOAc/hexane. Proton NMR for the product was consistent with the titled compound. HRMS (ES) exact mass calculated for $C_{22}H_{22}FN_2O_4$ (M+H$^+$): 397.1558. Found 397.1520.

HMQC NMR spectral data for the product were consistent with the titled compound. HRMS (ES) exact mass calculated for $C_{21}H_{17}FN_3O_4$ (M+H$^+$): 394.1198. Found 394.1202.

Example 9

2-Chloro-4-(3-fluorophenyl)-6-methoxyquinoline-3-carbonitrile

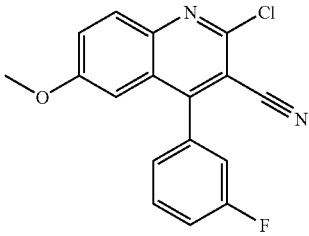

A solution of 4-(3-fluorophenyl)-6-methoxy-2-oxo-1,2-dihydroquinoline-3-carbonitrile (1.10 g, 3.74 mmol) in 30 mL of phosphorus oxytrichloride was heated in a sealed pressure tube at 90° C. for 2 hours. The solution was cooled to room temperature and allowed to stand overnight. The mixture was diluted with EtOAc, cooled to 0° C., and quenched by the careful addition of saturated NaHCO$_3$ solution. The organic phase was washed with brine, dried over Na$_2$SO$_4$, filtered, and concentrated in vacuo to provide the titled compound. ESI+ MS: 313.0 [M+H]$^+$.

Example 10

(2S)-2-[(2,3-Dihydroxypropyl)amino]-4-(3-fluorophenyl)-6-methoxyquinoline-3-carbonitrile

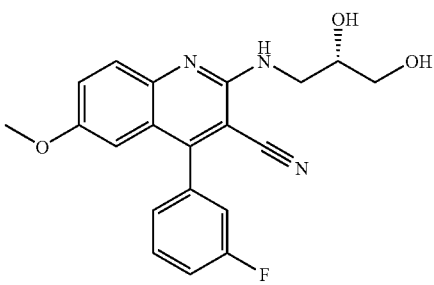

A solution of 2-chloro-4-(3-fluorophenyl)-6-methoxyquinoline-3-carbonitrile (65.0 mg, 0.208 mmol) and (S)-2,3-dihydroxypropylamine (114 mg, 1.25 mmol) in 10 mL of 2-propanol was heated in a sealed tube at 120° C. for 63 hours. Another portion of (S)-2,3-dihydroxypropylamine was added (50 mg), and the reaction was stirred for another 12 hours. The solution was concentrated in vacuo. The crude residue was purified by preparative reversed phase HPLC to provide the titled product. Proton NMR for the product was consistent with the titled compound. HRMS (ES) exact mass calculated for $C_{20}H_{19}FN_3O_3$ (M+H$^+$): 368.1405. Found 368.1398.

Example 11

(2R)-2-[(2,3-Dihydroxypropyl)amino]-4-(3-fluorophenyl)-6-methoxyquinoline-3-carbonitrile

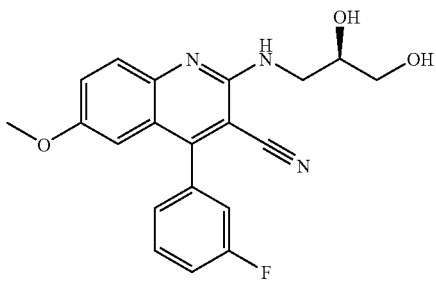

Following the procedure described in Example 10, replacing (S)-2,3-dihydroxypropylamine with (R)-2,3-dihydroxypropylamine, the titled compound was obtained after precipitation of the crude product from EtOAc/hexane, followed by trituration with EtOAc/hexane. Proton NMR for the product was consistent with the titled compound. HRMS (ES) exact mass calculated for $C_{20}H_{19}FN_3O_3$ (M+H$^+$): 368.1405. Found 368.1405.

Example 12

(3R,4R)-2-(3,4-Dihydroxypyrrolidin)-4-(3-fluorophenyl)-6-methoxyquinoline-3-carbonitrile

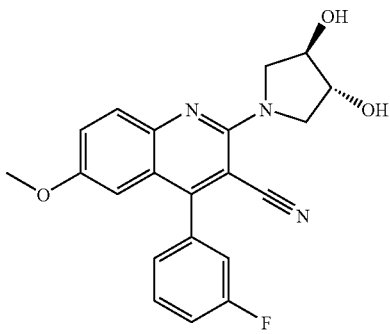

A solution of 2-chloro-4-(3-fluorophenyl)-6-methoxyquinoline-3-carbonitrile (61.0 mg, 0.20 mmol), (3R,4R)-3,4-dihydroxypyrrolidine (43 mg, 0.42 mmol) and triethylamine (0.055 mL, 0.42 mmol) in 3 mL of 2-propanol was heated in a sealed tube at 120° C. for 3 days. The temperature was raised to 150° C. After 3 days, additional portions of (3R,4R)-3,4-dihydroxypyrrolidine (40 mg) and triethylamine (0.055 mL) were added. After a total of 11 days, the solution was cooled and diluted with EtOAc. The organic layer was washed with saturated NaHCO$_3$ solution and brine, and dried over Na$_2$SO$_4$, filtered, and concentrated in vacuo. The crude residue was purified by recrystallization from EtOAc/hexane (40 mg, 54%). Proton NMR for the product was consistent with the titled compound. HRMS (ES) exact mass calculated for $C_{21}H_{19}FN_3O_3$ (M+H$^+$): 380.1405. Found 380.1401.

Example 13

(3S,4S)-2-(3,4-Dihydroxypyrrolidin-1-yl)-4-(3-fluorophenyl)-6-methoxyquinoline-3-carbonitrile

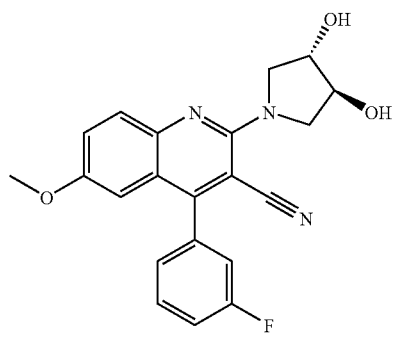

Following the procedure described in Example 12, replacing (3R,4R)-3,4-dihydroxypyrrolidine with (3S,4S)-3,4-dihydroxypyrrolidine, the titled compound was obtained. Proton NMR for the product was consistent with the titled compound. HRMS (ES) exact mass calculated for $C_{20}H_{19}FN_3O_3$ (M+H$^+$): 368.1405. Found 368.1401.

Example 14

4-(3-fluorophenyl)-6-methoxy-2-(4-methyl-1H-imidazol-1-yl)quinoline-3-carbonitrile

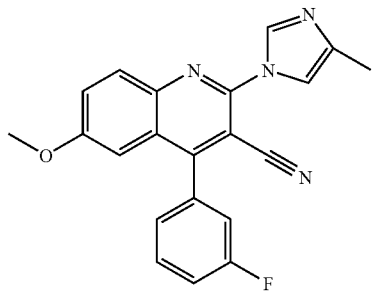

Following the procedure described in Example 12, replacing (3R,4R)-3,4-dihydroxypyrrolidine with 4-methylimidazole, and replacing triethylamine with N,N-diisopropylethylamine, the titled compound was obtained. Proton NMR for the product was consistent with the titled compound. $^1$H-NMR (500 MHz, d$_6$-DMSO) δ 8.30 (d, J=1.2 Hz, 1H), 8.09 (d, J=9.3 Hz, 1H), 7.75 (m, 1H), 7.72 (dd, J=9.3, 3.0 Hz, 1H), 7.61 (br s, 1H), 7.60 (m, 1H), 7.50-7.55 (m, 2H) 6.88 (d, J=2.7 Hz, 1H), 3.77 (s, 3H), 2.23 (s, 3H) ppm. HRMS (ES) exact mass calculated for $C_{21}H_{16}FN_4O$ (M+H$^+$): 359.1303. Found 359.1305.

Example 15

2-(Allyloxy)-4-(3-fluorophenyl)-6-methoxyquinoline-3-carbonitrile

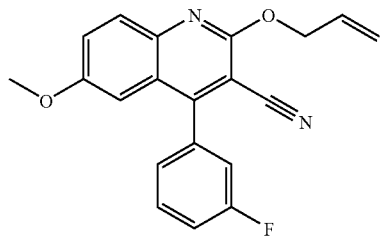

Step A: (2-Amino-5-methoxyphenyl)(3-fluorophenyl)methanone

To a 0° C. solution of para-anisidine (8.13 g, 66.0 mmol) in 25 mL of chlorobenzene was added dropwise a solution of $BCl_3$ in dichloromethane (74.3 mL of 1 M, 74.3 mmol). The mixture was stirred at room temperature for one hour, then transferred slowly via syringe to solution of 3-fluorobenzonitrile (4.00 g, 33.0 mmol) and $AlCl_3$ (5.06 g, 37.9 mmol) in 50 mL of chlorobenzene at 60° C. After the addition was complete, the reaction was stirred at 70° C. for 3 hours, then cooled to room temperature and stirred overnight. Water was added (125 mL), and the mixture stirred at 85 degrees for 6 hours. After cooling to room temperature, the mixture was poured into water, and the organic layer was extracted with saturated $NaHCO_3$ solution and brine, dried over $Na_2SO_4$, filtered, and concentrated in vacuo. The crude residue was purified by flash chomatography through $SiO_2$ (50-100% $CH_2Cl_2$/hexane) to provide the titled product (1.83 g, 23% yield) as a red oil. Proton NMR for the product was consistent with the titled compound. HRMS (ES) exact mass calculated for $C_{14}H_{13}FNO_2$ (M+H$^+$): 246.0929. Found 246.0925.

Step B: {2-[(2,4-Dimethoxybenzyl)amino]-5-methoxyphenyl}(3-fluorophenyl)methanone To a solution of (2-Amino-5-methoxyphenyl)(3-fluorophenyl)methanone (0.984 g, 4.01 mmol) in 15 mL of dichloroethane was added 4 Å powdered molecular sieves (1 g), followed by sodium triacetoxyborohydride (2.55 g, 12.0 mmol) and acetic acid (0.69 mL, 12.0 mmol). 2,4-Dimethoxybenzaldehyde was added (0.667 g, 4.01 mmol), and the reaction was stirred at room temperature for 3 hours. The reaction was partitioned between EtOAc and saturated $NaHCO_3$ solution, and the organic layer was washed with brine, dried over $Na_2SO_4$, filtered, and concentrated in vacuo. The titled product was isolated as a red oil (1.66 g) which was used in the next step without further purification. ESI+ MS: 396.2 [M+H]$^+$.

Step C: 2-Cyano-N-2,4-dimethoxybenzyl)-N-[2-(3-fluorobenzoyl)-4-methoxyphenyl]acetamide To a solution of cyanoacetic acid (43.0 mg, 0.511 mmol) in 1 mL of dichloromethane at room temperature was added $PCl_5$ (106 mg, 0.511 mmol). The mixture was heated to reflux for 10 minutes. A solution of {2-[(2,4-dimethoxybenzyl)amino]-5-methoxyphenyl}(3-fluorophenyl)methanone (101 mg, 0.255 mmol) in 1 mL dichloromethane was added, and the reaction was refluxed for an additional 1.5 hours. The reaction was partitioned between EtOAc and saturated $NaHCO_3$ solution, and the organic layer was washed with brine, dried over $Na_2SO_4$, filtered, and concentrated in vacuo. The titled product was isolated as a yellow foam (117 mg, 99% yield) which was used in the next step without further purification. Proton NMR for the product was consistent with the titled compound. ESI+ MS: 463.2 [M+H]$^+$.

Step D: 1-(2,4-Dimethoxybenzyl)-4-(3-fluorophenyl)-6-methoxy-2-oxo-1,2-dihydroquinoline-3-carbonitrile To solution of 2-cyano-N-(2,4-dimethoxybenzyl)-N-[2-3-fluorobenzoyl)-4-methoxyphenyl]acetamide (56.0 mg, 0.121 mmol) in 1 mL of methanol was added sodium methoxide solution in methanol (0.083 mL of 4.37 M, 0.363 mmol). The solution was heated to reflux for 5 minutes, then cooled to room temperature. The reaction was partitioned between EtOAc and water, and the organic layer was washed with brine, dried over $Na_2SO_4$, filtered, and concentrated in vacuo. The crude residue was purified by flash chomatography through $SiO_2$ (30-50% EtOAc/hexane) to provide the titled product (51 mg, 95% yield) as a yellow foam. $^1$H-NMR (500 MHz, CDCl$_3$) δ 7.56-7.60 (m, 1H), 7.39 (d, J=9.5 Hz, 1H), 7.25-7.31 (m, 2H), 7.17-7.21 (m, 2H), 6.91 (d, J=8.5 Hz, 1H), 6.74 (br s, 1H), 6.52 (br s, 1H), 6.38 (br d, J=8.5 Hz, 1H), 5.54 (s, 2H), 3.95 (s, 3H), 3.77 (s, 3H), 3.67 (s, 3H) ppm. HRMS (ES) exact mass calculated for $C_{26}H_{22}FN_2O_4$ (M+H$^+$): 445.1558. Found 445.1574.

Step E: 4-(3-Fluorophenyl)-6-methoxy-2-oxo-1,2-dihydroquinoline-3-carbonitrile To a solution of 1-2,4-dimethoxybenzyl)-4-(3-fluorophenyl)-6-methoxy-2-oxo-1,2-dihydroquinoline-3-carbonitrile (42 mg, 0.094 mmol) in 0.5 mL of dichloromethane and 1 mL of trifluoroacetic acid was added dimethyl sulfide (0.10 mL). After stirring for 2 days, the reaction was heated to reflux for 10 hours, then concentrated in vacuo. The crude product was triturated with EtOAc to provide the titled product as a pale yellow solid. Proton NMR for the product was consistent with the titled compound. HRMS (ES) exact mass calculated for $C_{17}H_{11}FN_2O_2$ (M+H$^+$): 295.0878. Found 295.0879.

Step F: 2(Allyloxy)-4-(3-fluorophenyl)-6-methoxyquinoline-3-carbonitrile

To a solution of 4-(3-fluorophenyl)-6-methoxy-2-oxo-1,2-dihydroquinoline-3-carbonitrile (1.00 g, 3.40 mmol) in 20 mL of N,N-dimethylformamide at 0° C. was added sodium hydride (163 mg of 60% dispersion in mineral oil, 4.08 mmol). After 30 minutes, allyl iodide was added (0.342 mL, 3.74 mmol), and the reaction was stirred for 2 hours. The reaction was quenched with water and partitioned between EtOAc and water, and the organic layer was washed with brine, dried over $Na_2SO_4$, filtered, and concentrated in vacuo. The crude residue was subjected to flash chomatography through $SiO_2$ (5-60% EtOAc/hexane) to provide the second eluting product as the titled compound (151 mg, 13% yield). $^1$H NMR, difference nOe, and HMQC NMR spectral data for the product were consistent with the titled compound. ESI+ MS: 335.1 [M+H]$^+$.

Example 16

(±)-2-(2,3-Dihydroxypropoxy)-4-(3-fluorophenyl)-6-methoxyquinoline-3-carbonitrile, enantiomer A

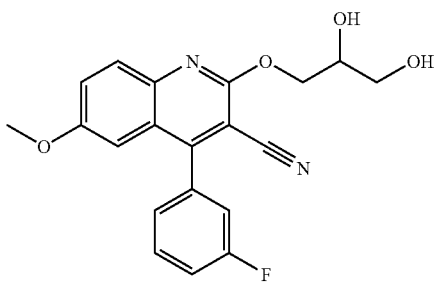

To a solution of 2-(allyloxy)-4-(3-fluorophenyl)-6-methoxyquinoline-3-carbonitrile (140 mg, 0.419 mmol) in 10 mL of tBuOH:THF:water (10:3:1) was added N-methylmorpholine N-oxide (49 mg, 0.42 mmol), followed by a solution of OsO4 (106 mg, 0.42 mmol) in water (ca. 0.5 mL). After stirring for 18 hours, the reaction was diluted with EtOAc, washed with saturated NaHCO$_3$ solution, 10% citric acid solution and brine, and the organic layer was dried over Na$_2$SO$_4$, filtered, and concentrated in vacuo. The crude residue (144 mg) was subjected to preparative chiral HPLC through a Chiralcel OD column (85% hexanes containing 0.1% diethylamine:EtOH). The first eluting peak was collected and concentrated in vacuo to provide the titled product. $^1$H-NMR (500 MHz, CDCl$_3$) δ 7.81 (d, J=9.0 Hz, 1H), 7.70 (ddd, J=8.1, 8.1, 5.6 Hz, 1H), 7.44 (dd, J=9.0, 2.9 Hz, 1H), 7.30 (ddd, J=8.6, 2.4, 1.0 Hz, 1H), 7.25 (m, 1H), 7.19 (br d, J=8.6 Hz, 1H), 6.83 (d, J=2.9 Hz, 1H), 4.68-4.76 (m, 2H), 4.19 (m, 1H), 3.84 (dd, J=11.6, 4.1 Hz, 1H), 3.79 (dd, J=11.6, 5.4 Hz, 1H), 3.74 (s, 3H) ppm. HRMS (ES) exact mass calculated for C$_{20}$H$_{18}$FN$_2$O$_4$ (M+H$^+$): 369.1245. Found 369.1195.

Example 17

(±)-2-(2,3-Dihydroxypropoxy)-4-(3-fluorophenyl)-6-methoxyquinoline-3-carbonitrile, enantiomer B

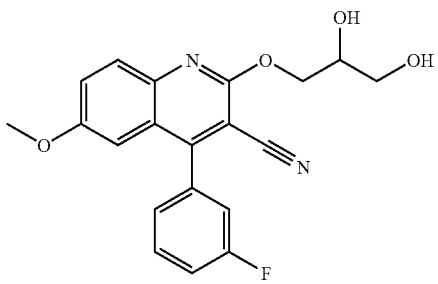

The crude residue from Example 16 was subjected to preparative chiral HPLC through a Chiralcel OJ column (85% hexanes containing 0.1% diethylamine:EtOH). The second eluting peak was collected and concentrated in vacuo to provide the titled product. Proton NMR for the product was consistent with the titled compound. HRMS (ES) exact mass calculated for C$_{20}$H$_{15}$FN$_2$O$_4$ (M+H$^+$): 369.1245. Found 369.1239.

Example 18

4-(3-Fluorophenyl)-6-methoxy-2-[(3-pyridin-3-yl-1,2,4-oxadiazol-5-yl)methoxy]quinoline-3-carbonitrile

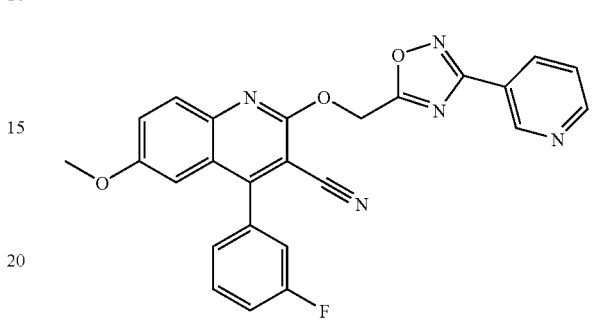

Following the procedure described in Step F of Example 15, replacing allyl iodide with 5-chloromethyl-3-pyridin-3-yl)-1,2,4-oxadiazole, the titled compound was obtained as the first eluting product after purification by flash chromatography through silica gel (EtOAc:hexane). Proton NMR for the product was consistent with the titled compound. $^1$H NMR, difference nOe, and HMQC NMR spectral data for the product were consistent with the titled compound. HRMS (ES) exact mass calculated for C$_{25}$H$_{17}$FN$_5$O$_3$ (M+H$^+$): 454.1310. Found 454.1313.

Example 19

4-(3-Fluorophenyl)-6-methoxy-2-[(3-pyridin-3-yl)methoxy]quinoline-3-carbonitrile

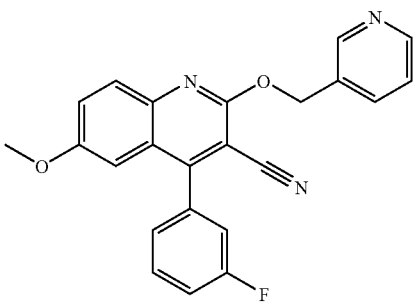

To a solution of 4-(3-fluorophenyl)-6-methoxy-2-oxo-1,2-dihydroquinoline-3-carbonitrile (50.0 mg, 0.170 mmol) in 2 mL of 1,2-dimethoxyethane and 0.5 mL of N,N-dimethylformamide at 0° C. was added sodium hydride (10.0 mg of 60% dispersion in mineral oil, 0.26 mmol). After 10 minutes, lithium bromide was added (30 mg, 0.34 mmol), and the reaction was stirred for one hour. 2-(Chloromethyl)pyridine hydrochloride (33 mg, 0.17 mmol) was added, and the reaction was allowed to warm to room temperature. After 18 hours, another portion of sodium hydride (10.0 mg of 60% dispersion in mineral oil, 0.26 mmol) was added. After 24 hours, the reaction was quenched with water and partitioned between EtOAc and water, and the organic layer was washed with brine, dried over Na$_2$SO$_4$, filtered, and concentrated in vacuo. The titled compound was obtained as the second eluting product after purification by preparative reversed phase HPLC. Proton NMR for the product was consistent with the titled compound. $^1$H NMR, difference nOe, and HMQC NMR spectral data for the product were consistent with the titled compound. HRMS (ES) exact mass calculated for C$_{23}$H$_{17}$FN$_3$O$_2$ (M+H$^+$): 386.1299. Found 386.1303.

Example 20

(±)-4-(3-Fluorophenyl)-6-methoxy-2-[(2-oxo-1,3-oxazolidin-5-yl)methoxy]quinoline-3-carbonitrile

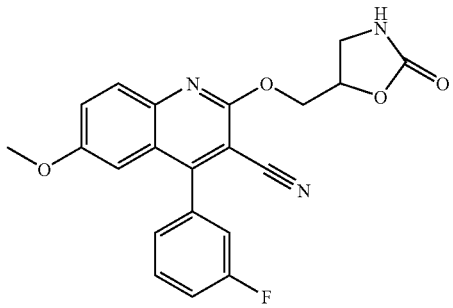

Following the procedure described in Step F of Example 15, replacing allyl iodide with 5-(chloromethyl)-1,3-oxazolidin-2-one, and heating the reaction in a pressure tube at 120° C. for 16 hours, the titled compound was obtained after purification by preparative reversed phase HPLC (first eluting product). $^1$H NMR, difference nOe, COSY, HMBC and HMQC NMR spectral data for the product were consistent with the titled compound. HRMS (ES) exact mass calculated for C$_{21}$H$_{17}$FN$_3$O$_4$ (M+H$^+$): 394.1198. Found 394.1202.

Example 21

4-(3-Fluorophenyl)-6-methoxy-2-(pent-4-enyloxy)quinoline-3-carbonitrile

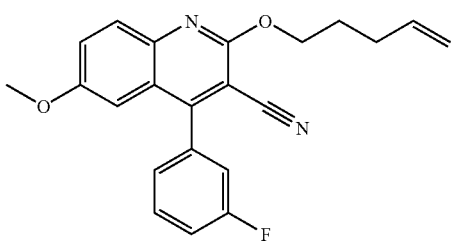

Following the procedure described in Step F of Example 15, replacing allyl iodide with 5-bromopentene, the titled compound was obtained after purification by crystallization from EtOAc/hexane, followed by further purification by preparative reversed phase HPLC (first eluting product). $^1$H NMR, difference nOe, and HMQC NMR spectral data for the product were consistent with the titled compound. HRMS (ES) exact mass calculated for C$_{22}$H$_{20}$FN$_2$O$_2$ (M+H$^+$): 363.1504. Found 363.1500.

Example 22

(±)-2-[(4,5-Dihydroxypentyl)oxy]-4-(3-fluorophenyl)-6-methoxyquinoline-3-carbonitrile

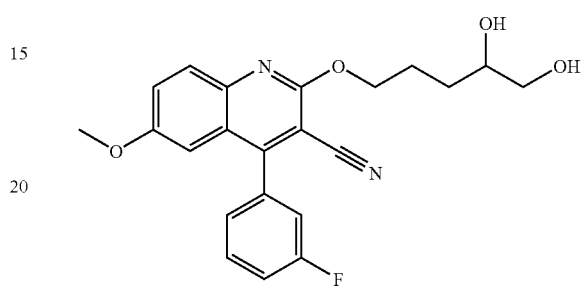

Following the procedure described in Example 16, replacing 2-(allyloxy)-4-(3-fluorophenyl)-6-methoxyquinoline-3-carbonitrile with 4-(3-fluorophenyl)-6-methoxy-2-(pent-4-enyloxy)quinoline-3-carbonitrile, the titled compound was obtained after precipitation of the crude product from EtOAc/hexane. Proton NMR for the product was consistent with the titled compound. HRMS (ES) exact mass calculated for C$_{22}$H$_{22}$N$_2$O$_4$ (M+H$^+$): 397.1558. Found 397.1520.

Example 23

2-Chloro-4-(3-fluorophenyl)-6-methoxyquinoline-3-carbonitrile

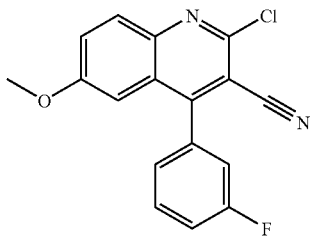

A solution of 4-(3-fluorophenyl)-6-methoxy-2-oxo-1,2-dihydroquinoline-3-carbonitrile (1.10 g, 3.74 mmol) in 30 mL of phosphorus oxytrichloride was heated in a sealed pressure tube at 90° C. for 2 hours. The solution was cooled to room temperature and allowed to stand overnight. The mixture was diluted with EtOAc, cooled to 0° C., and quenched by the careful addition of saturated NaHCO$_3$ solution. The organic phase was washed with brine, dried over Na$_2$SO$_4$, filtered, and concentrated in vacuo to provide the titled compound (774 mg, 66%) ESI+ MS: 313.0 [M+H]$^+$.

Example 24

(2S)-2-[(2,3-Dihydroxypropyl)amino]-4-(3-fluorophenyl)-6-methoxyquinoline-3-carbonitrile

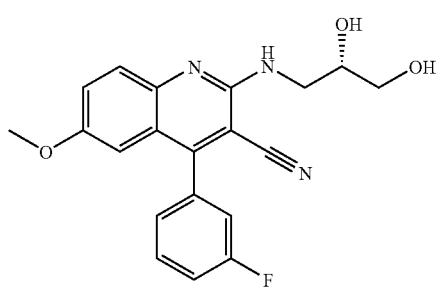

A solution of 2-chloro-4-(3-fluorophenyl)-6-methoxyquinoline-3-carbonitrile (65.0 mg, 0.208 mmol) and (S)-2,3-dihydroxypropylamine (114 mg, 1.25 mmol) in 10 mL of 2-propanol was heated in a sealed tube at 120° C. for 63 hours. Another portion of (S)-2,3-dihydroxypropylamine was added (50 mg), and the reaction was stirred for another 12 hours. The solution was concentrated in vacuo. The crude residue was purified by preparative reversed phase HPLC to provide the titled product (17 mg, 22%). Proton NMR for the product was consistent with the titled compound. HRMS (ES) exact mass calculated for $C_{20}H_{19}FN_3O_3$ (M+H$^+$): 368.1405. Found 368.1398.

Example 25

(2R)-2-[(2,3-Dihydroxypropyl)amino]-4-(3-fluorophenyl)-6-methoxyquinoline-3-carbonitrile

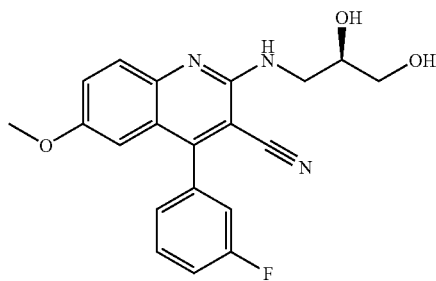

Following the procedure described in Example 24, replacing (S)-2,3-dihydroxypropylamine with (R)-2,3-dihydroxypropylamine, the titled compound was obtained after precipitation of the crude product from EtOAc/hexane, followed by trituration with EtOAc/hexane. Proton NMR for the product was consistent with the titled compound. HRMS (ES) exact mass calculated for $C_{21}H_{19}FN_3O_3$ (M+H$^+$): 368.1405. Found 368.1405.

Example 26

(3R,4R)-2-(3,4-Dihydroxypyrrolidin-1-yl)-4-(3-fluorophenyl)-6-methoxyquinoline-3-carbonitrile

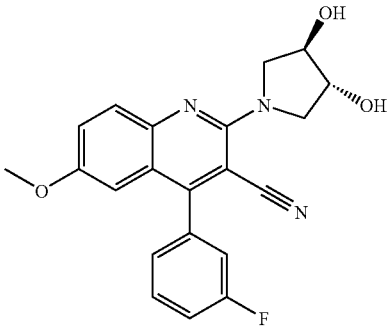

A solution of 2-chloro-4-(3-fluorophenyl)-6-methoxyquinoline-3-carbonitrile (61.0 mg, 0.20 mmol), (3R,4R)-3,4-dihydroxypyrrolidine (43 mg, 0.42 mmol) and triethylamine (0.055 mL, 0.42 mmol) in 3 mL of 2-propanol was heated in a sealed tube at 120° C. for 3 days. The temperature was raised to 150° C. After 3 days, additional portions of (3R,4R)-3,4-dihydroxypyrrolidine (40 mg) and triethylamine (0.055 mL) were added. After a total of 11 days, the solution was cooled and diluted with EtOAc. The organic layer was washed with saturated NaHCO$_3$ solution and brine, and dried over Na$_2$SO$_4$, filtered, and concentrated in vacuo. The crude residue was purified by recrystallization from EtOAc/hexane (40 mg, 54%). Proton NMR for the product was consistent with the titled compound. HRMS (ES) exact mass calculated for $C_{21}H_{19}FN_3O_3$ (M+M$^+$): 380.1405. Found 380.1401.

Example 27

(3S,4S)-2-(3,4-Dihydroxypyrrolidin-1-yl)-4-(3-fluorophenyl)-6-methoxyquinoline-3-carbonitrile

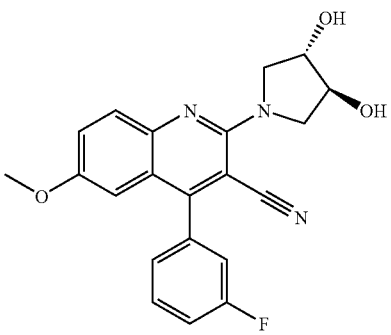

Following the procedure described in Example 26, replacing (3R,4R)-3,4-dihydroxypyrrolidine with (3S,4S)-3,4-dihydroxypyrrolidine, the titled compound was obtained. Proton NMR for the product was consistent with the titled compound. HRMS (ES) exact mass calculated for $C_{20}H_{19}FN_3O_3$ (M+H$^+$): 368.1405. Found 368.1401.

Example 28

4-(3-fluorophenyl)-6-methoxy-2-(4-methyl-1H-imidazol-1-yl)quinoline-3-carbonitrile

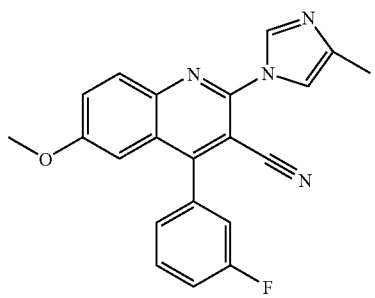

Following the procedure described in Example 26, replacing (3R,4R)-3,4-dihydroxypyrrolidine with 4-methylimidazole, and replacing triethylamine with N,N-diisopropylethylamine, the titled compound was obtained. Proton NMR for the product was consistent with the titled compound. $^1$H-NMR (500 MHz, d$_6$-DMSO) δ 8.30 (d, J=1.2 Hz, 1H), 8.09 (d, J=9.3 Hz, 1H), 7.75 (m, 1H), 7.72 (dd, J=9.3, 3.0 Hz, 1H), 7.61 (br s, 1H), 7.60 (m, 1H), 7.50-7.55 (m, 2H) 6.88 (d, J=2.7 Hz, 1H), 3.77 (s, 3H), 2.23 (s, 3H) ppm. HRMS (ES) exact mass calculated for $C_{21}H_{16}FN_4O$ (M+H$^+$): 359.1303. Found 359.1305.

The following compounds were made according to the procedures analogous to those described above, where intermediates were modified according to literature methods. Example 45 was made from Example 35 by reaction with dimethyl chlorophosphate and titanium tert-butoxide followed by demethylation with dimethylsulfide and methanesulfonic acid.

Examples 29-45

Examples 29-45 are shown in the table below. Unless the structure is shown completely, the examples have the following structure with variable XX$_1$ defined in the table.

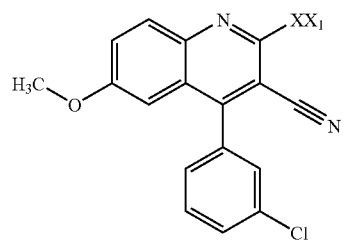

| Example | Compound | Name | MS (M + 1) |
|---|---|---|---|
| 29 | ![structure] | 4-(3-fluorophenyl)-6-methoxy-2-(pent-4-enyloxy)quinoline-3-carbonitrile | 363.1471 |
| 30 | ![structure] | 2-[(4,5-dihydroxypentyl)oxy]-4-(3-fluorophenyl)-6-methoxyquinoline-3-carbonitrile | 397.1520 |

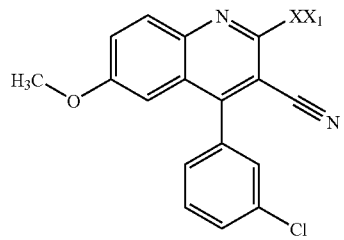

| Example | Compound | Name | MS (M + 1) |
|---|---|---|---|
| 31 | | 4-(3-fluorophenyl)-6-methoxy-2-[(2-morpholin-4-ylethyl)amino]quinoline-3-carbonitrile | 407.1833 |
| 32 | | 2-chloro-4-(3-fluorophenyl)-6-methoxyquinoline-3-carbonitrile | 313.16 (m + 1) |
| 33 | | 4-(3-fluorophenyl)-6-methoxy-2-{[2-(4-methylpiperazin-1-yl)ethyl]amino}quinoline-3-carbonitrile | 420.2201 |
| 34 | XX₁ is —Cl | 2-chloro-4-(3-chlorophenyl)-6-methoxyquinoline-3-carbonitrile | 329.0247 |
| 35 | XX₁ is —NH—CH₂CH₂—OH | 4-(3-chlorophenyl)-2-[(2-hydroxyethyl)amino]-6-methoxyquinoline-3-carbonitrile | 354.1003 |
| 36 | XX₁ is —NH—CH₂-(tetrahydrofuran-2-yl) | 4-(3-chlorophenyl)-6-methoxy-2-[(tetrahydrofuran-2-ylmethyl)amino]quinoline-3-carbonitrile | 394.1323 |
| 37 | XX₁ is —NH—(CH₂)₄—CH(NH₂)—COOH | (1S)-1-carboxy-5-{[4-(3-chlorophenyl)-3-cyano-6-methoxyquinolin-2-yl]amino}pentan-1-amine hydrochloride | 439.1506 |

-continued

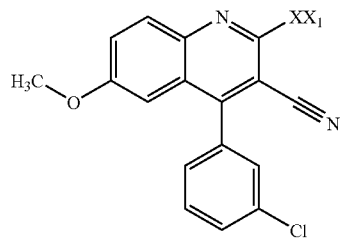

| Example | Compound | Name | MS (M + 1) |
|---|---|---|---|
| 38 | XX₁ is —N(CH₃)₂ | 4-(3-chlorophenyl)-2-(dimethylamino)-6-methoxyquinoline-3-carbonitrile | 338.1037 |
| 39 | XX₁ is —NHCH₂C(O)N(CH₃)₂ | 2-{[4-(3-chlorophenyl)-3-cyano-6-methoxyquinolin-2-yl]amino}-N,N-dimethylacetamide | 395.1256 |
| 40 | XX₁ is —NH₂ | 2-amino-4-(3-chlorophenyl)-6-methoxyquinoline-3-carbonitrile | 310.0733 |
| 41 | XX₁ is (3S)-3-amino-2-oxopyrrolidin-1-yl | 2-[(3S)-3-amino-2-oxopyrrolidin-1-yl]-4-(3-chlorophenyl)-6-methoxyquinoline-3-carbonitrile | 393.1107 |
| 42 | XX₁ is —F | 4-(3-chlorophenyl)-2-fluoro-6-methoxyquinoline-3-carbonitrile | 313.0546 |
| 43 | XX₁ is 1,1-dioxidothiomorpholin-4-yl | 4-(3-chlorophenyl)-2-(1,1-dioxidothiomorpholin-4-yl)-6-methoxyquinoline-3-carbonitrile | 428.0851 |
| 44 | XX₁ is pyrrolidin-1-yl | 4-(3-chlorophenyl)-6-methoxy-2-pyrrolidin-1-ylquinoline-3-carbonitrile | 364.1197 |
| 45 | XX₁ is —NHCH₂CH₂OP(O)(OH)₂ | 2-{[4-(3-chlorophenyl)-3-cyano-6-methoxyquinolin-2-yl]amino}ethyl dihydrogen phosphate | 434.2 |

Using the methodologies described below, representative compounds of the invention were evaluated and found to exhibit activity in the Kv1.5 assays, thereby demonstrating and confirming the utility of the compounds of this invention as Kv1.5 inhibitors and antiarrhythmics. Compounds of this type may exhibit forward rate-dependence, blocking the outward $K^+$ currents to a greater extent or preferentially at faster rates of depolarization or heart rates. Such a compound could be identified in electrophysiological studies as described below. For example, during a train of depolarizations delivered at frequencies of 1 Hz and 3 Hz, the block is "rate-dependent" if the amount of block observed during a 10 second train at 3 Hz is greater than that at 1 Hz. A Kv1.5 blocker may also display use-dependence, during which the block of the outward K+ currents increases with use, or during repetitive depolarization of a cardiac cell. Use dependence of block occurs to a greater extent with each successive depolarization in a train or sequence of pulses or depolarizations at a given rate or frequency. For example, during a train of 10 depolarizations at a frequency of 1 Hz, the block is "use-dependent" if the amount of block is greater for the $10^{th}$ pulse than for the $1^{st}$ pulse of the train. A Kv1.5 blocker may exhibit both use-dependence and rate-dependence.

A Kv1.5 blocker may also be identified through electrophysiological studies of native $I_{Kur}$ using cardiac myocytes or other tissue from various species including, but not limited to, human, rat, mouse, dog, monkey, ferret, rabbit, guinea pig, or goat. In native tissues Kv1.5 may exist as a homo-oligomer, or as a hetero-oligomer with other Kv family members, or may exist in a complex with a β-subunit. Compounds of this invention may block Kv1.5 homo- or hetero-oligomers or Kv1.5 in complexes with β-subunits.

Kv1.5 Assays

The high throughput Kv1.5 planar patch clamp assay is a systematic primary screen. It confirms activity and provides a functional measure of the potency of agents that specifically affect Kv1.5 potassium channels. Kiss et al. (Assay and Drug Dev. Tech., 1(1-2):127-135,2003) and Schroeder et al. (J. of Biomol. Screen., 8(1); 50-64, 2003) describe the use of this instrument for Kv 1.5 as well as other voltage gated ion channels.

Chinese hamster ovary cells (CHO) stably expressing the human Kv1.5 potassium channel alpha subunit, cloned from human heart, are grown to 90-100% confluence in Ham's F12 medium supplemented with 10% FBS, 100 U/ml penicillin, 100 µg/ml streptomycin, 1000 µg/ml G-418 sulfate. Cells are subcultured by treatment with Versene, then suspended in phosphate-buffered saline (PBS) and centrifuged The cell pellet is resuspended in PBS and the resulting suspension placed in the cell reservoir of the IonWorks™ HT instrument.

Electrophysiological recordings are performed with intracellular solution containing (mM): K-gluconate 100, KCl 40, MgCl$_2$ 3.2, EGTA 3, N-2-hydroxyethylpiperazine-N$^1$-2-ethanesulphonic acid (HEPES) 5, adjusted to pH 7.3. Amphotericin (Sigma) is prepared as 30 mg/ml stock solution and diluted to a final working concentration of 0.1 mg/ml in internal buffer solution. The external solution is Dulbecco's PBS (Invitrogen) and contains (mM): CaCl$_2$ 0.90, KCl 2.67, KPO$_4$ 1.47, MgCl$_2$ 0.50, NaCl 138, NaPO$_4$ 8.10 and has a pH of 7.4. All compounds are prepared as 10 mM stock solutions in DMSO. Compounds are diluted into external buffer, then transferred from the drug plate to the Patchplate during the experiment (final DMSO concentration <0.66% vol.).

Kv1.5 ionic currents are recorded at room temperature. Membrane currents are amplified (RMS ~10 pA) and sampled at 10 kHz. Leak subtraction was performed in all experiments by applying a 160 ms hyperpolarizing (10 mV) pre-pulses 200 ms before the test pulses to measure leak conductance. The patch clamp stimulus protocol is as follows:

1. Patchplate wells are loaded with 3.5 µL of external buffer.
2. Planar micropipette hole resistances (Rp) is determined by applying a 10 mV, 160 ms potential difference across each hole (Hole test).
3. Cells are pipetted into the Patchplate and form high resistance seals with the 1-2 µm holes at the bottom of each Patchplate well. A seal test scan is performed to determine how many of the Patchplate wells have cells that have formed seals.
4. In order to gain electrical access to the cells, intracellular solution containing amphotericin is circulated for 4 minutes on the bottom side of the Patchplate.
5. Pre-compound addition test pulse is applied to each well on the Patchplate. Protocol: Cells are voltage clamped at a membrane holding potential of −80 mV for 15 seconds. This is followed by application of a 5 Hz stimulus train (27×150 ms depolarizations to +40 mV). The membrane potential steps to +40 mV evoke outward (positive) ionic currents.
6. Compound is added to each well of the Patchplate. Compounds are allowed to incubate for 5 minutes.
7. Post-compound addition test pulse protocol is applied. Protocol: Cells are voltage clamped at a membrane holding potential of −80 mV for 15 seconds. This is followed by application of a 5 Hz stimulus train (27×150 ms depolarizations to +40 mV).

Data analysis is conducted off-line. Paired comparisons between pre-drug and post-drug additions are used to determine the inhibitory effect of each compound. % inhibition of the peak control current during the $27^{th}$ depolarization to +40 mV (in the 5 Hz train) is plotted as a function of antagonist concentration. The concentrations of drug required to inhibit current by 50% (IC$_{50}$) are determined by fitting of the Hill equation to the concentration response data: % of Control=$100 \times (1+([Drug]/IC_{50})^p)^{-1}$ For each cell four arithmetic metrics are obtained:
1) seal resistance
2) baseline metric (the mean current at −70 mV from 5 to 45 ms before the first depolarization to +40 mV)
3) current run up metric (pre-compound mean current amplitude during the $1^{st}$ depolarization to +40 mV minus the pre-compound mean current amplitude during the $27^{th}$ depolarization to +40 mV)
4) peak current (maximum current amplitude during the $27^{th}$ depolarization to +40 mV during the 5 Hz train).

All metrics are obtained during both the pre- and post-compound addition traces. Cells are eliminated from further analysis if:
1) seal resistance is <50 MΩ
2) baseline metric is >±100 pA during the pre-compound
3) current run up metric is >−0.2 nA
4) pre-read peak metric is <400 pA.

The above-listed compounds provide >20% inhibition at a concentration of 33 µM or less in the high throughput Kv1.5 planar patch clamp assay described above.

Atomic Absorption Spectroscopy Protocol:

This assay identifies agents that specifically block the human Kv1.5 K+ channel heterologously expressed in CHO cells as measured by Rb+ efflux using Flame Atomic Absorption Spectroscopy (FAAS). The application of FAAS for measuring ion channel activity was adapted from Terstappen et al, *Anal. Biochem.*, 272:149-155, 1999.

CHO cells expressing human Kv1.5 are cultured as described above, then harvested with trypsin-EDTA and washed with medium.
1. 40,000 cells per well are seeded in a 96-well cell culture plate (assay plate) and the cells are allowed to grow for 48 hours at 37° C.
2. The medium is removed and 200 µl of Rb Load Buffer (Aurora Biomed, Vancouver, BC) is added for 3 hours at 37° C. under 5% CO$_2$.

3. The cells are washed 5 times with 200 μl Hank's Balanced Salt Solution (HBSS) followed by the addition of 100 μl HBSS containing test compound or 0.5% DMSO.
4. After 10 min, 100 μl of HEPES-buffered saline containing 140 mM KCl is added and plate is incubated at RT for 5 min. with gentle shaking.
5. Immediately thereafter, 150 μl of supernatant is transferred to a fresh 96 well plate and the remaining supernatant aspirated.
6. 120 μl of Cell Lysis Buffer (Aurora Biomed, Vancouver, BC) is added to the assay plate and shaken for 10 min. prior to analysis.
7. Rb content is measured in samples of supernatant (SUP) and lysate (LYS) using an ICR-8000 automated AAS instrument (Aurora Biomed, Vancouver, BC).

% FLUX=100%*(SUP/(LYS+SUP)). % INH=100%*(1−(A−B)/(C−B)), where A is % FLUX in the presence of tested compound, B is % FLUX in the presence of 10 mM (6-methoxy-2-methyl-1-oxo-4-phenyl-1,2-dihydroisoquinolin-3-yl)-N,N-dimethylmethanaminium chloride, C is % FLUX in the presence of 0.25% DMSO.

The above-listed compounds provide ≧25% inhibition at a concentration of 25 μM or less in the AAS assay described above.

The compounds of this invention can be administered for the treatment or prevention of afflictions, diseases and illnesses according to the invention by any means that effects contact of the active ingredient compound with the site of action in the body of a warm-blooded animal. For example, administration, can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1-500 milligrams per day. Ordinarily, from 10 to 100 milligrams per day in one or more applications is effective to obtain desired results. These dosages are the effective amounts for the treatment and prevention of afflictions, diseases and illnesses described above, e.g., cardiac arrhythmias such as atrial fibrillation, atrial flutter, atrial arrhythmia, and supraventricular tachycardia, thromboembolic events such as stroke and congestive heart failure, and immunodepression.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Compounds of the invention can be administered as the sole active ingredient or in combination with a second active ingredient, including other antiarrhythmic agents having Kv1.5 blocking activities such as quinidine, propafenone, ambasilide, amiodarone, flecainide, sotalol, bretylium, dofetilide, almokalant, bepridil, clofilium, other compounds having Kv1.5 blocking activities such as clotrimazole, ketoconazole, bupivacaine, erythromycin, verapamil, nifedipine, zatebradine, bisindolylmaleimide, or other cardiovascular agents such as, but not limited to, ACE inhibitors such as benazepril, captopril, enalapril, fosinopril, lisinopril, moexipril, perindopril erbumine, quinapril, ramipril, and trandolapril, angiotensin II antagonists such as candesartan, eprosartan, irbesartan, losartan, olmesartan, telmisartan, and valsartan, cardiac glycosides such as digoxin, L-type calcium channel blockers, T-type calcium channel blockers, selective and nonselective beta blockers, an immunosuppresant compound, endothelin antagonists, thrombin inhibitors, aspirin, nonselective NSAIDs other than aspirin such as naproxen, warfarin, factor Xa inhibitors, low molecular weight heparin, unfractionated heparin, clopidogrel, ticlopidine, IIb/IIIa receptor antagonists such as tirofiban, 5HT receptor antagonists, integrin receptor antagonists, thromboxane receptor antagonists, TAFI inhibitors and P2T receptor antagonists. Compounds of the invention can also be administered as the sole active ingredient or in combination with a pacemaker or defibrillator device.

What is claimed is:

1. A compound of the structure:

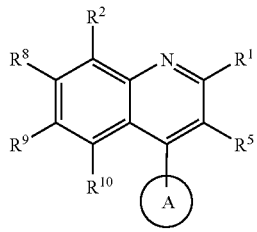

I or a pharmaceutically acceptable salt thereof, wherein

A is fluorophenyl or chlorophenyl;

$R^1$ is selected from the group consisting of —OCH$_2$CHCH$_2$, —OCH$_2$CH(OH)CH$_2$OH, —O(CH$_2$)$_3$CHCH$_2$, —OCH$_3$, —O(CH$_2$)$_3$CH(OH)CH$_2$OH, Cl, —NHCH$_2$CH$_2$OH, —NHCH$_2$CH(OH)CH$_2$OH, —NHCH$_2$CH(OH)CH$_2$OH,

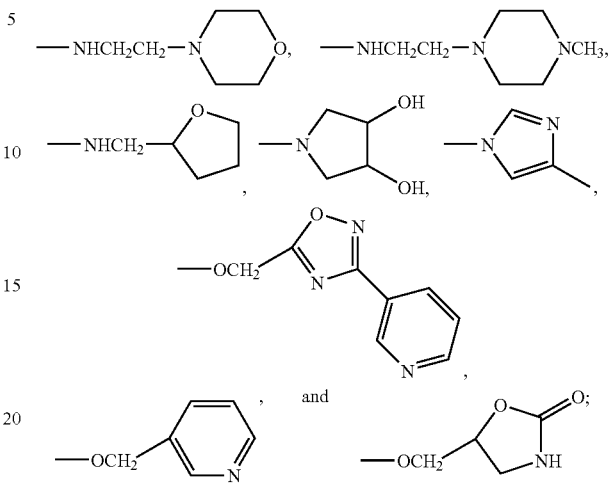

$R^2$, $R^8$ and $R^{10}$ are hydrogen, and $R^9$ is —OCH$_3$, wherein said compound is selected from the group consisting of 2-(Allyloxy)-4-(3-fluorophenyl)-6-methoxyquinoline-3-carbonitrile, (±)-2-(2,3-Dihydroxypropoxy)-4-(3-fluorophenyl)-6-methoxyquinoline-3-carbonitrile, 4-(3-Fluorophenyl)-6-methoxy-2-[(3-pyridin-3-yl-1,2,4-oxadiazol-5-yl)methoxy]quinoline-3-carbonitrile, 4-(3-Fluorophenyl)-6-methoxy-2-[(3-pyridin-3-yl)methoxy]quinoline-3-carbonitrile, (±)-4-(3-Fluorophenyl)-6-methoxy-2-[(2-oxo-1,3-oxazolidin-5-yl)methoxy]quinoline-3-carbonitrile, 4-(3-Fluorophenyl)-6-methoxy-2-(pent-4-enyloxy)quinoline-3-carbonitrile, (±)-2-[(4,5-Dihydroxypentyl)oxy]-4-(3-fluorophenyl)-6-methoxyquinoline-3-carbonitrile, 2-Chloro-4-(3-fluorophenyl)-6-methoxyquinoline-3-carbonitrile, 2-Chloro-4-(3-chlorophenyl)-6-methoxyquinoline-3-carbonitrile, (2S)-2-[(2,3-Dihydroxypropyl)amino]-4-(3-fluorophenyl)-6-methoxyquinoline-3-carbonitrile (2R)-2-[(2,3-Dihydroxypropyl)amino]-4-(3-fluorophenyl)-6-methoxyquinoline-3-carbonitrile, (3R,4R)-2-(3,4-Dihydroxypyrrolidin-1-yl)-4-(3-fluorophenyl)-6-methoxyquinoline-3-carbonitrile, (3S,4S)-2-(3,4-Dihydroxypyrrolidin-1-yl)-4-(3-fluorophenyl)-6-methoxyquinoline-3-carbonitrile, 4-(3-fluorophenyl)-6-methoxy-2-(4-methyl-1H-imidazol-1-yl)quinoline-3-carbonitrile, 2-(2-(N-morpholinyl)ethylamino)-6-methoxy-4-(3-fluorophenyl)quinoline-3-carbonitrile, 2-(2-(4-methylpiperidin-1-yl)ethylamino)-6-methoxy-4-(3-fluorophenyl)quinoline-3-carbonitrile, 2-(2-hydroxyethylamino)-6-methoxy-4-(3-chlorophenyl)quinoline-3-carbonitrile, 2-(tetrahydrofuranyl methylamino)-6-methoxy-4-(3-chlorophenyl)quinoline-3-carbonitrile, 2-(Allyloxy)-4-(3-fluorophenyl)-6-methoxyquinoline-3-carbonitrile, (±)-2-(2,3-Dihydroxypropoxy)-4-(3-fluorophenyl)-6-methoxyquinoline-3-carbonitrile, 4-(3-Fluorophenyl)-6-methoxy-2-[(3-pyridin-3-yl-1,2,4-oxadiazol-5-yl)methoxy]quinoline-3-carbonitrile, 4-(3-Fluorophenyl)-6-methoxy-2-[(3-pyridin-3-yl)methoxy]quinoline-3-carbonitrile, (±)-4-(3-Fluorophenyl)-6-methoxy-2-[(2-oxo-1,3-oxazolidin-5-yl)methoxy]quinoline-3-carbonitrile, 4-(3-Fluorophenyl)-6-methoxy-2-(pent-4-enyloxy)quinoline-3-carbonitrile, (±)-2-[(4,5-Dihydroxypentyl)

oxy]-4-(3-fluorophenyl)-6-methoxyquinoline-3-carbonitrile, 2-Chloro-4-(3-fluorophenyl)-6-methoxyquinoline-3-carbonitrile, (2S)-2-[(2,3-Dihydroxypropyl)amino]-4-(3-fluorophenyl)-6-methoxyquinoline-3-carbonitrile, (2R)-2-[(2,3-Dihydroxypropyl)amino]-4-(3-fluorophenyl)-6-methoxyquinoline-3-carbonitrile, (3R,4R)-2-(3,4-Dihydroxypyrrolidin-1-yl)-4-(3-fluorophenyl)-6-methoxyquinoline-3-carbonitrile, (3S,4S)-2-(3,4-Dihydroxypyrrolidin-1-yl)-4-(3-fluorophenyl)-6-methoxyquinoline-3-carbonitrile, and 4-(3-fluorophenyl)-6-methoxy-2-(4-methyl-1H-imidazol-1-yl)quinoline-3-carbonitrile, or a pharmaceutically acceptable salt thereof.

2. A pharmaceutical formulation comprising a pharmaceutically acceptable carrier and the compound of claim 1 or a pharmaceutically acceptable crystal form thereof.

3. A pharmaceutical composition made by combining the compound of claim 1 and a pharmaceutically acceptable carrier.

* * * * *